United States Patent
Ries et al.

(10) Patent No.: US 8,998,997 B2
(45) Date of Patent: *Apr. 7, 2015

(54) IMPLANTABLE MOBILE BEARING PROSTHETICS

(75) Inventors: Michael D. Ries, Tiburon, CA (US);
Mark Mooradian, Phoenix, AZ (US);
Daniel F. Justin, Orlando, FL (US);
Joshua A. Butters, Chandler, AZ (US)

(73) Assignee: Michael D. Ries, Tiburon, CA (US)

( * ) Notice: Subject to any disclaimer, the term of this patent is extended or adjusted under 35 U.S.C. 154(b) by 589 days.

This patent is subject to a terminal disclaimer.

(21) Appl. No.: 12/914,799

(22) Filed: Oct. 28, 2010

(65) Prior Publication Data
US 2011/0270403 A1    Nov. 3, 2011

Related U.S. Application Data

(63) Continuation-in-part of application No. 12/606,326, filed on Oct. 27, 2009, now Pat. No. 8,906,105.

(60) Provisional application No. 61/233,081, filed on Aug. 11, 2009, provisional application No. 61/255,566, filed on Oct. 28, 2009.

(51) Int. Cl.
*A61F 2/38*   (2006.01)
*A61F 2/30*   (2006.01)

(52) U.S. Cl.
CPC ............... *A61F 2/3868* (2013.01); *A61F 2/385* (2013.01); *A61F 2/3886* (2013.01); *A61F 2002/30616* (2013.01); *A61F 2002/30878* (2013.01); *A61F 2002/30884* (2013.01)

(58) Field of Classification Search
USPC .......................................... 623/20.27, 20.33
See application file for complete search history.

(56) References Cited

U.S. PATENT DOCUMENTS

| 1,372,918 A | 3/1921 | Udgaard |
| 4,211,228 A | 7/1980 | Cloutier |

(Continued)

FOREIGN PATENT DOCUMENTS

| DE | 202010000037 | 3/2010 |
| EP | 1378216 | 1/2004 |

(Continued)

OTHER PUBLICATIONS

Dennis; Douglas A., et al. *A Multicenter Analysis of Axial Femorotibial Rotation after Total Knee Arthroplasty.* Clinical Orthopaedics and Related Research No. 428, pp. 180-189 (2004).

(Continued)

*Primary Examiner* — Bruce E Snow
*Assistant Examiner* — Melissa Hoban
(74) *Attorney, Agent, or Firm* — Snell & Wilmer L.L.P.

(57) ABSTRACT

A knee prosthesis including a femoral implant, a tibial implant, a tibial insert and a cam post. The femoral implant is secured to a femur and has a gap for receiving a natural PCL. The tibial implant is secured to a tibia. The tibial insert comprises a medial cavity with a rotational axis. The tibial insert has articulating surfaces that match the contours of the condyles of the femoral implant and a notch for retaining the natural PCL. The tibial insert has a medial boss that aligns with the medial cavity allowing it to rotate about the rotational axis. A post is secured to the tibial implant and enters a hole of the tibial insert providing anterior and posterior stops for the rotation of the tibial insert about the rotational axis.

13 Claims, 41 Drawing Sheets

(56) References Cited

U.S. PATENT DOCUMENTS

| | | | |
|---|---|---|---|
| 4,213,209 A | 7/1980 | Insall | |
| 4,224,697 A | 9/1980 | Murray | |
| 4,634,444 A | 1/1987 | Noiles | |
| 4,714,472 A | 12/1987 | Khowaylo | |
| 4,936,853 A | 6/1990 | Fabian et al. | |
| 5,047,058 A | 9/1991 | Roberts | |
| 5,071,438 A | 12/1991 | Jones | |
| 5,071,738 A | 12/1991 | Mizikura | |
| 5,330,533 A | 7/1994 | Walker | |
| 5,330,534 A | 7/1994 | Herrington | |
| 5,370,701 A | 12/1994 | Finn | |
| 5,387,240 A | 2/1995 | Pottenger | |
| 5,413,604 A | 5/1995 | Hodge | |
| 5,480,446 A | 1/1996 | Goodfellow | |
| 5,658,342 A | 8/1997 | Draganich | |
| 5,702,464 A | 12/1997 | Lackey et al. | |
| 5,755,801 A | 5/1998 | Walker | |
| 5,755,804 A | 5/1998 | Schmotzer et al. | |
| 5,824,102 A | 10/1998 | Buscayret | |
| 5,879,392 A | 3/1999 | McMinn | |
| 5,879,394 A | 3/1999 | Ashby | |
| 5,906,643 A | 5/1999 | Walker | |
| 5,928,286 A | 7/1999 | Ashby | |
| 5,976,147 A | 11/1999 | LaSalle et al. | |
| 6,013,103 A | 1/2000 | Kaufman | |
| 6,039,764 A | 3/2000 | Pottenger | |
| 6,080,195 A | 6/2000 | Colleran | |
| 6,099,570 A | 8/2000 | Livet et al. | |
| 6,159,216 A | 12/2000 | Burkinshaw et al. | |
| 6,165,223 A | 12/2000 | Cox | |
| 6,203,576 B1 | 3/2001 | Afriat | |
| 6,214,052 B1 | 4/2001 | Burkinshaw | |
| 6,296,666 B1 | 10/2001 | Gardner | |
| 6,387,111 B1 | 5/2002 | Barber | |
| 6,413,279 B1 | 7/2002 | Cox | |
| 6,428,577 B1 | 8/2002 | Evans | |
| 6,558,427 B2 | 5/2003 | Leclercq | |
| 6,592,588 B1 | 7/2003 | Bobic | |
| 6,620,168 B1 | 9/2003 | Lombardo et al. | |
| 6,629,999 B1 | 10/2003 | Serafin, Jr. | |
| 6,645,215 B1 | 11/2003 | McGovern et al. | |
| 6,764,516 B2 | 7/2004 | Pappas | |
| 6,773,461 B2 | 8/2004 | Meyers et al. | |
| 6,797,005 B2 | 9/2004 | Pappas | |
| 6,972,039 B2 | 12/2005 | Metzger | |
| 6,974,481 B1 | 12/2005 | Carson | |
| 6,986,791 B1 | 1/2006 | Metzger | |
| 7,001,394 B2 | 2/2006 | Gundlapalli | |
| 7,105,027 B2 | 9/2006 | Lipman et al. | |
| 7,232,465 B2 | 6/2007 | Keller | |
| 7,328,634 B1 | 2/2008 | Greenberg et al. | |
| 7,422,605 B2 | 9/2008 | Burstein et al. | |
| 7,572,292 B2 | 8/2009 | Crabtree | |
| 7,658,767 B2 | 2/2010 | Wyss | |
| 7,691,150 B2 | 4/2010 | Cronin et al. | |
| 8,137,407 B2 | 3/2012 | Todd et al. | |
| 2001/0003803 A1 | 6/2001 | Leclercq | |
| 2003/0009229 A1 | 1/2003 | Pappas | |
| 2003/0009232 A1 | 1/2003 | Hoeppner | |
| 2003/0153980 A1 | 8/2003 | Brack | |
| 2003/0199985 A1 | 10/2003 | Masini | |
| 2004/0097951 A1 | 5/2004 | Steffensmeier | |
| 2004/0243244 A1 | 12/2004 | Ries | |
| 2005/0021039 A1 | 1/2005 | Cusick et al. | |
| 2005/0149045 A1 | 7/2005 | Elliott | |
| 2005/0203528 A1 | 9/2005 | Couture et al. | |
| 2005/0209701 A1 | 9/2005 | Kuramoto | |
| 2005/0209702 A1 | 9/2005 | Todd | |
| 2006/0064104 A1 | 3/2006 | Kana et al. | |
| 2006/0149276 A1 | 7/2006 | Grimm | |
| 2006/0161259 A1 | 7/2006 | Huang | |
| 2006/0184176 A1 | 8/2006 | Straszheim-Morley et al. | |
| 2006/0190086 A1 | 8/2006 | Clemow | |
| 2007/0100462 A1 | 5/2007 | Lang | |
| 2007/0100463 A1 | 5/2007 | Aram | |
| 2007/0129808 A1 | 6/2007 | Justin et al. | |
| 2007/0135925 A1 | 6/2007 | Walker | |
| 2007/0135926 A1 | 6/2007 | Walker | |
| 2007/0173848 A1 | 7/2007 | Lennox et al. | |
| 2007/0173856 A1 | 7/2007 | Parker | |
| 2008/0009950 A1 | 1/2008 | Richardson | |
| 2008/0021566 A1 | 1/2008 | Peters | |
| 2008/0027555 A1 | 1/2008 | Hawkins | |
| 2008/0097616 A1 | 4/2008 | Meyers | |
| 2008/0114464 A1 | 5/2008 | Barnett | |
| 2008/0119940 A1 | 5/2008 | Otto | |
| 2008/0188943 A1 | 8/2008 | Smith | |
| 2008/0195109 A1 | 8/2008 | Hunter et al. | |
| 2008/0243259 A1 | 10/2008 | Lee | |
| 2008/0300690 A1 | 12/2008 | Burstein | |
| 2009/0043395 A1 | 2/2009 | Takano | |
| 2009/0043396 A1 | 2/2009 | Komistek | |
| 2009/0088861 A1 | 4/2009 | Tuke | |
| 2009/0090220 A1 | 4/2009 | Kimberly | |
| 2009/0149964 A1 | 6/2009 | May | |
| 2009/0210066 A1 | 8/2009 | Jasty | |
| 2009/0299482 A1 | 12/2009 | Metzger et al. | |
| 2009/0326665 A1 | 12/2009 | Gomaa | |
| 2009/0326666 A1 | 12/2009 | Bennett | |
| 2009/0326668 A1 | 12/2009 | Dun | |
| 2010/0010635 A1 | 1/2010 | Straszheim-Morley et al. | |
| 2010/0016978 A1 | 1/2010 | Gomaa | |
| 2010/0016979 A1 | 1/2010 | Gomaa | |
| 2010/0042224 A1 | 2/2010 | Garino | |
| 2010/0049200 A1 | 2/2010 | Re | |
| 2010/0312351 A1 | 12/2010 | Belcher | |

FOREIGN PATENT DOCUMENTS

| | | |
|---|---|---|
| JP | 2008062030 | 3/2008 |
| WO | WO9525484 | 9/1995 |
| WO | WO9603097 | 2/1996 |
| WO | WO9613233 | 5/1996 |
| WO | WO9846171 | 10/1998 |
| WO | WO0113825 | 3/2001 |
| WO | 0182842 | 11/2001 |
| WO | WO0234156 | 5/2002 |
| WO | 03059203 | 7/2003 |
| WO | WO2006118822 | 11/2006 |
| WO | WO2008045863 | 4/2008 |
| WO | WO2011059759 | 5/2011 |

OTHER PUBLICATIONS

Dennis; Douglas A. et al: *Factors Affecting Flexion After Total Knee Arthroplasty*. Clinical Orthopedics and Related Research, No. 464, pp. 53-60 (2007).

Argenson; Jean-Noel A.: *In Vivo Kinematic Evaluation and Design Considerations Related to High Flexion in Total Knee Arthroplasty*. Journal of Biomechanics 38 (2005) pp. 227.284.

Halloran; Jason P. et al.: *Explicit Finite Element Modeling of Total Knee Replacement Mechanics*, Journal of Biomechanics 38 (2005) pp. 323-331.

Morra; Edward A., et al.: The Influence *of Contemporary Knee Design on High Flexion II: A Kinematic Comparison with the Normal Knee*. Orthopaedic Research Laboratories Cleveland, Ohio, (2009).

Greenwald; Seth A., et al.: *Mobile-Bearing Knee Systems: Ultra-High Molecular Weight Polyethylene Wear and Design Issues*. AAOS Instructional Course Lectures, vol. 54 (2005) pp. 195-205.

Vertullo; Christopher J., et al.: *Mobile Bearing in Primary Knee Arthroplasty*. Journal of the American Academy of Orthopaedic Surgeons, vol. 9, No. 6, Nov./Dec. 2001 pp. 335-364.

Morra, Edward A., et al.: *Polymer Insert Stress in Total Knee Designs During High Flexion Activities*. A Finite Element Study, Orthopaedic Research Laboratories (2005) AAOS.

Catani, Fabio, et al.: *In Vivo Kinematics of Guided Motion Total Knee Arthroplasty*. Smith & Nephew, Poster # 1987 at the 2008 ORS Annual Meeting, San Francisco, CA.

Smith & Nephew: *Bi-Cruciate Stabilized Knee System* Journey Knee (2006) www.journeyknee.com.

(56) References Cited

OTHER PUBLICATIONS

Biomet AGC Total Knee System: Product Brochure May (2009) http://www.biomet.com.
Biomet Europe: *ALPINA APR Total Knee Prosthesis* (2007) http://www.biomet.co.uk/index.php?id=17313.
Biomet Europe: *Oxford TMK* (2007) http://www.biomet.co.uk/index.php?id=185&PHPSESSID=3b5253f8b4.
Biomet Europe: *Vanguard Complete Knee System*. Product Brochure (May 2009) http://www.biomet.co.uk.
Consensus Orthopedics: *Mobile Bearing Knee*. Product Brochure (2009) www.consensusortho.com.
Corin Group: Total Knee Replacement. Product Brochure (Jan. 20, 2011) http://www.coringroup.com/medical_professionals/products/knees/.
Depuy Orthopaedics Inc: *Finsbury; Dual Bearing Knee (DBK)* (2010) (http://www.finsbury.org/printer_friendly_version.asp?contentID=50.
DePuy: *LCS Complete Knee System*. (2011) pp. 1-2 http://www.depuy.com/healthcare-professionals/product-details/lcs-complete-knee-system.
Depuy Orthopaedics Inc: *Sigma Rotating Platform Knee System*. © 2008-2009 DePuy Orthopaedics, Inc. Product Brochure. (May 2009) http://www.depuy.com/healthcare-professionals/product-details.
Akagi; Masao: *A Mechanical Comparison of 2 Posterior-Stabilizing Designs; Insall/Burstein 2 Knee and Bisurface Knee*. The Journal of Arthroplasty vol. 17 No. 5 pp. 627-634 (2002).
Smith & Nephew: Journey Bi-Cruciate Stabilized Knee System. Product Brochure May 2009.
Sonstegard; DA: *The Spherocentric Knee: Biomechanical Testing and Clinical Trial*. The Journal of Bone & Joint Surgery (1977) vol. 59 pp. 602-616 Website: www.jbjs.org.
Stryker Orthopaedics: *Scorpio NRG (The Evolution of a High Performance Knee System)* Product Brochure (2007) Website: www.stryker.com.
Wright Medical: *Advance Knee System*. Family Product Brochure (2006) Website: www.wmt.com
Zimmer: *Comprehensive Natural-Knee Family*. (2006) Website: http://www.zimmer.co.uk/z/ctl/op/global/action/1/id/7802/template/MP.
Zimmer: *Gender Solutions Natural-Knee Flex System*. Product Brochure (2007) Website: www.zimmer.com.
Zimmer: The Comprehensive Natural-Knee Family (2007) Website: http://www.zimmer.co.uk/z/ctl/op/global/action/1/id/7802/template/MP
Zimmer: *NexGen Complete Knee Solutions*. Product Brochure: #97-5972-205 (2000-2001).
Zimmer: *NexGen LPS-Flex Mobile and LPS-Mobile Bearing Knee*. Advertisement (2008) #97-5964-017-00.
Restriction Requirement dated Nov. 26, 2012 in U.S. Appl. No. 12/949,073.
Office Action dated Jan. 23, 2013 in U.S. Appl. No. 12/949,073.
Notice of Allowance dated Jun. 26, 2013 in U.S. Appl. No. 12/949,073.
Restriction Requirement dated Sep. 20, 2012 in U.S. Appl. No. 12/951,832.
Office Action dated Oct. 26, 2012 in U.S. Appl. No. 12/951,832.
Notice of Allowance dated Apr. 12, 2013 in U.S. Appl. No. 12/951,832.
Restriction Requirement dated Jul. 1, 2011 in U.S. Appl. No. 12/606,326.
Office Action dated Aug. 19, 2011 in U.S. Appl. No. 12/606,326.
Restriction Requirement dated Nov. 7, 2012 in U.S. Appl. No. 12/949,103.
Office Action dated Jan. 22, 2013 in U.S. Appl. No. 12/949,103.
Final Office Action dated Sep. 12, 2013 in U.S. Appl. No. 12/949,103.
Office Action dated Nov. 5, 2014 in U.S. Appl. No. 12/949,103.
Restriction Requirement dated Apr. 9, 2012 in U.S. Appl. No. 12/949,153.
Office Action dated May 22, 2012 in U.S. Appl. No. 12/949,153.
Notice of Allowance dated Oct. 22, 2012 in U.S. Appl. No. 12/949,153.
Corrected Notice of Allowance dated Nov. 20, 2012 in U.S. Appl. No. 12/949,153.
Restriction Requirement dated Sep. 19, 2012 in U.S. Appl. No. 13/188,699.
Office Action dated Oct. 25, 2012 in U.S. Appl. No. 13/188,699.
Final Office Action dated Apr. 18, 2013 in U.S. Appl. No. 13/188,699.
Notice of Allowance dated Oct. 29, 2013 in U.S. Appl. No. 13/188,699.
International Search Report dated Oct. 21, 2011 in Application No. PCT/US2011/045019.
Written Opinion dated Oct. 21, 2011 in Application No. PCT/US2011/045019.
International Preliminary Report on Patentability dated Oct. 21, 2011 in Application No. PCT/US2011/045019.
International Search Report dated Feb. 14, 2011 in Application No. PCT/US2012/036289.
Written Opinion dated Feb. 14, 2011 in Application No. PCT/US2012/036289.
International Preliminary Report on Patentability dated Feb. 14, 2012 in Application No. PCT/US2012/036289.
International Search Report dated Aug. 2, 2011 in Application No. PCT/US2010/054534.
Written Opinion dated Aug. 2, 2011 in Application No. PCT/US2010/054534.
International Preliminary Report on Patentability dated May 1, 2012 in Application No. PCT/US2010/054534.
International Search Report dated Aug. 18, 2011 in Application No. PCT/US2010/057231.
Written Opinion dated Aug. 18, 2011 in Application No. PCT/US2010/057231.
International Preliminary Report on Patentability dated May 22, 2012 in Application No. PCT/US2010/057231.
International Search Report dated Aug. 22, 2011 in Application No. PCT/US2010/057642.
Written Opinion dated Aug. 22, 2011 in Application No. PCT/US2010/057642.
International Preliminary Report on Patentability dated May 30, 2012 in Application No. PCT/US2010/057642.
Walker; Peter s.: Biomechanical Principles of Total Knee Replacement Design. Basic Orthpaedic Biomechanics 2nd edition, 1997, pp. 1-493.
Pria; P. Dalla, et al.: Ceramic Knee Design 11th Symposium Session 4.3, 2006, pp. 115-124.
Orthopedics, Feature Article; Sep. 2006 vol. 29, No. 9 Supplement, pp. S17-S22.
Final Office Action dated Jan. 27, 2012 in U.S. Appl. No. 12/606,326.
Banks; Scott, et al.: Knee Motions During Maximum Flexion in Fixed and Mobile-Bearing Arthroplasti;cs. Clinical Orthopeadics and Related Research No. 410, 2003, pp. 131-138.
Exam Report dated Dec. 3, 2014 in European Application No. 11738916.3.
Office Action dated Jul. 11, 2014 in U.S. Appl. No. 12/606,326.
Notice of Allowance dated Oct. 27, 2014 in U.S. Appl. No. 12/606,326.

IMPLANTABLE MOBILE BEARING PROSTHETICS

CROSS-REFERENCE TO RELATED APPLICATIONS

This application is a continuation in part of U.S. patent application Ser. No. 12/606,326 filed 27 Oct. 2009, and is entitled SYSTEMS AND METHODS FOR MOBILE BEARING PROSTHETIC KNEE, which is incorporated herein by reference in its entirety, which claims the benefit of the filing date of U.S. Provisional Application No. 61/233,081, and is entitled MOBILE BEARING PROSTHETIC KNEE, which is incorporated herein by reference in its entirety.

This application also claims priority to U.S. Provisional Application No. 61/255,566 filed 28 Oct. 2009, and is entitled CRUCIATE RETAINING MOBILE BEARING PROSTHETIC KNEE, which is incorporated herein by reference in its entirety.

BACKGROUND

One attribute of normal knee flexion is that, as the knee flexes, the contact points of the femur on the tibia move posteriorly. This posterior movement of the contact points is known as rollback. Also, normal knee rollback is much more pronounced on the lateral side of the knee than the medial side, which results in femoral external rotation during knee flexion. Rollback is facilitated by the natural posterior cruciate ligament (PCL). With prosthetic knees, as the knee flexes, the PCL causes a femoral implant of a prosthesis and femur to move in a posterior direction.

Other prosthetic knees currently on the market do not use two separate fully guided motion paths, and as a consequence may not reproduce normal knee kinematics and need to use wear components made of polyethylene, or similar material, to accommodate the less-guided sliding that occurs during knee flexion. These existing methods and procedures may not be as effective as desired. There is a need to have a tibial insert of a prosthetic knee roll back on a medial pivot axis causing greater rollback on the lateral side than the medial side, like a normal, non-prosthetic knee.

BRIEF DESCRIPTION OF THE DRAWINGS

Various embodiments of the present device will now be discussed with reference to the appended drawings. It is appreciated that these drawings depict only typical embodiments of the device and are therefore not to be considered limiting of its scope. It is further understood that individual characteristics of the various embodiments may be combined to form further embodiments without departing from the scope of the device.

DETAILED DESCRIPTION

The application relates to systems and methods used in orthopaedic surgery, and in particular, to total knee arthroplasty. Those of skill in the art will recognize that the systems and methods described herein may be readily adapted for any total joint arthroplasty procedure. Those of skill in the art will also recognize that the following description is merely illustrative of the principles of the device, which may be applied in various ways to provide many different alternative embodiments. This description is made for the purpose of illustrating the principles of this device and is not meant to limit the inventive concepts in the appended claims.

Figure 1:
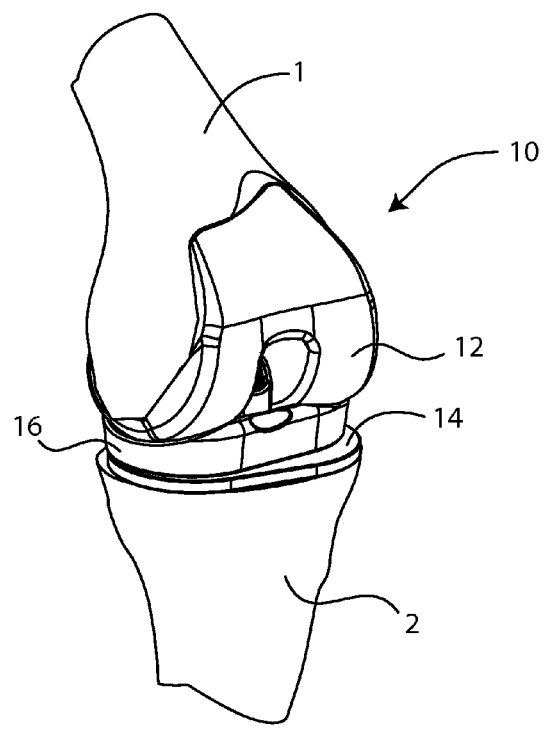
FIG. 1 illustrates a perspective view of the prosthesis, with a femur, a tibia, a tibial baseplate, a tibial insert, a femoral implant and a reference arrow diagram.
Figure 1:
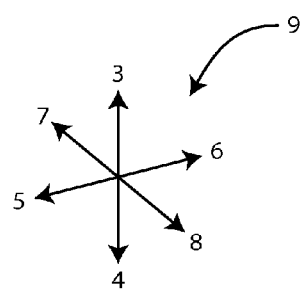

Referring to FIG. 1, a perspective view illustrates a mobile bearing prosthesis 10 according to one embodiment, implanted in a knee. This figure and subsequent figures may be oriented according to the reference arrow diagram 9, having a superior direction 3, an inferior direction 4, a medial direction 5, a lateral direction 6, a posterior direction 7, and an anterior direction 8. In this application, "left" and "right" are used with reference to a posterior view. "Medial" refers to a position or orientation toward a sagittal plane (i.e., plane of symmetry that separates left and right sides of the body from each other), and "lateral" refers to a position or orientation relatively further from the sagittal plane. The prosthesis 10 may comprise a tibial baseplate 14, a tibial insert 16 and femoral implant 12.

Figure 2:
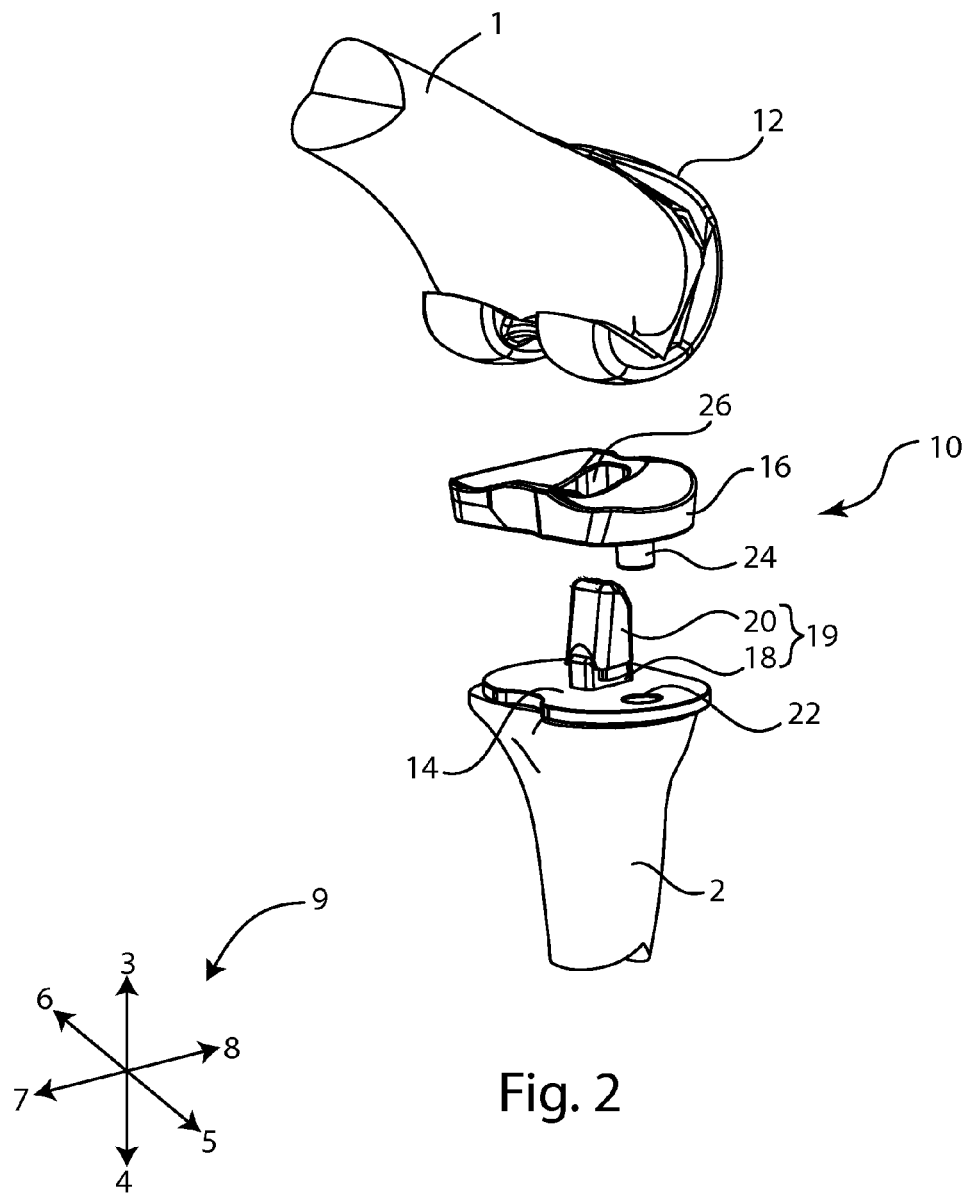
FIG. 2 illustrates an exploded perspective view of the prosthesis of FIG. 1 with the femur, the tibia, the tibial baseplate with a tibial baseplate aperture, the tibial insert with a tibial insert boss and a tibial insert hole, the femoral implant, and a cam post with an outer sleeve.
Figure 3:
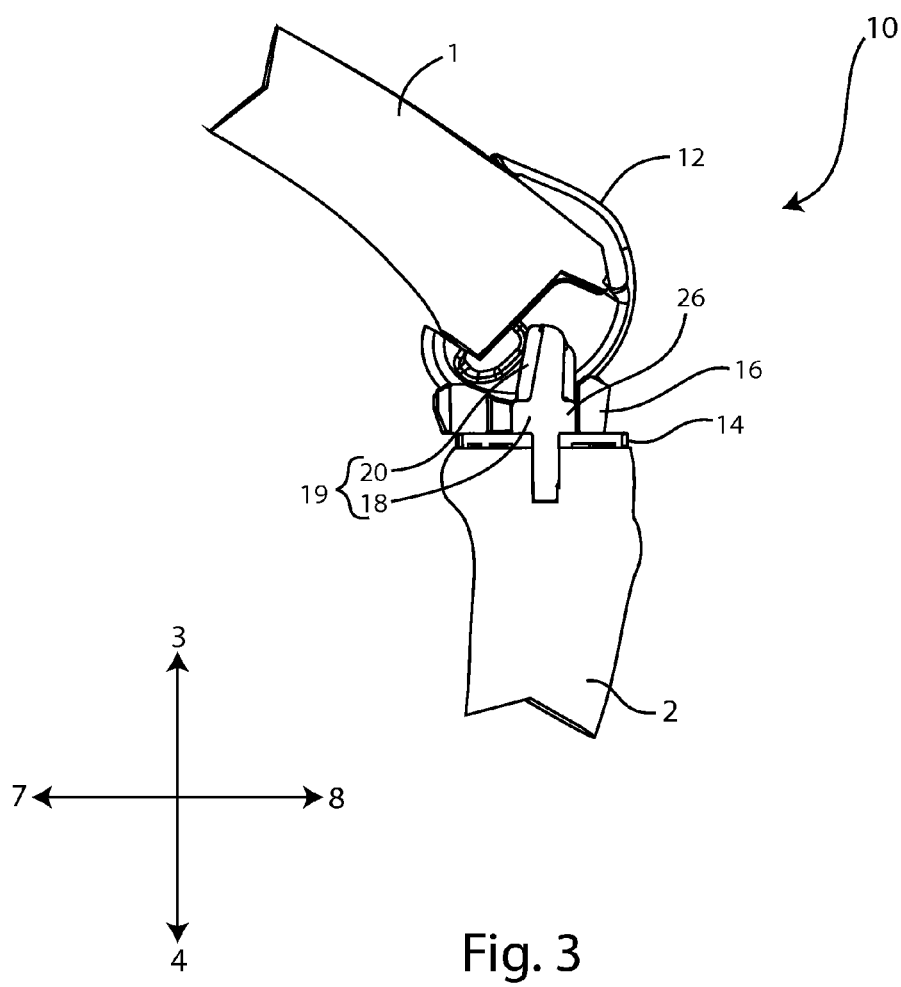
FIG. 3 illustrates a cross sectional side view of the prosthesis of FIG. 1 with the femur, tibia, tibial implant, tibial insert, femoral implant, and the cam post with the outer sleeve.

Referring to FIGS. 2 and 3, the prosthesis 10 comprises the tibial baseplate 14, attached to the resected tibia 2; a cam post 19 may be attached to the tibial baseplate 14 and may either be a modular or non-modular part of the baseplate. The cam post 19 helps guide the rotation of the femoral component and tibial insert 16 during flexion of the prosthesis 10. The cam post 19 of this embodiment is of two-piece construction, with a cam post core 18, which may be metallic, and a sleeve 20, which may be a polymer outer wear sleeve. However, either the cam post core 18 or the sleeve 20 may be comprised of other biocompatible materials. A tibial insert 16 may be rotationally connected to the tibial baseplate 14, rotating about an axis within a tibial insert channel 26 which axis of rotation is medial to the midline of the tibia. A femoral implant 12 may be attached to a resected femur 1, which is supported by the tibial insert 16 and which slidably engages with the cam post 19 to guide the rotation of the tibial insert and posterior movement of the femoral component 16 during flexion of the prosthesis 10.

For any of the parts of the prosthetic knee any biocompatible material may be used, including but not limited to stainless steels, titanium and its alloys, cobalt-chrome and its alloys, ceramics, composite materials, and polymers.

Figure 4:
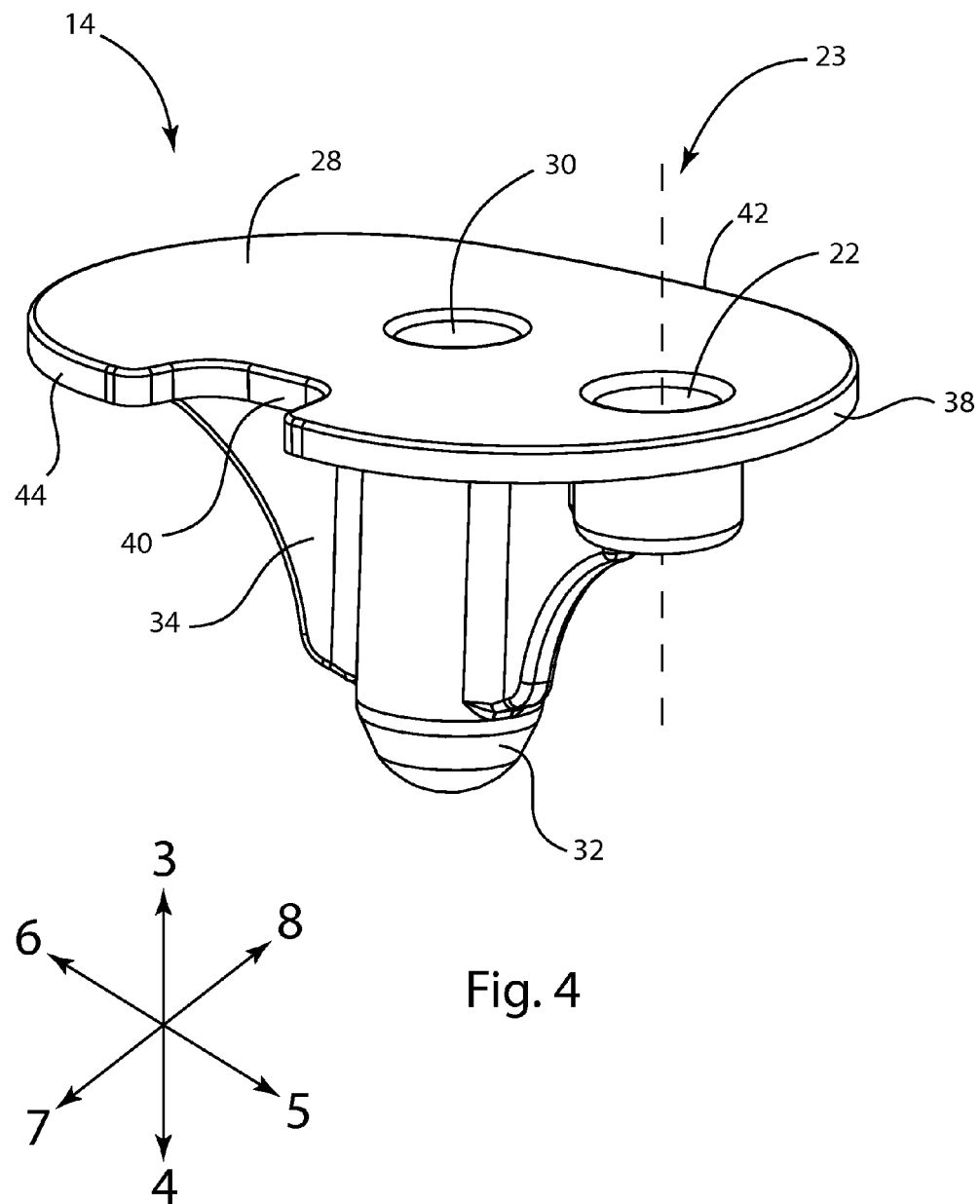
FIG. 4 illustrates a perspective top view of one embodiment of the tibial baseplate of FIG. 1 with the tibial baseplate cavity for retention of a boss of the tibial insert, and a tibial baseplate hole for passage of the cam post, on a tibial baseplate bearing surface, a keel extending into the tibia and at least one wing.
Figure 5:
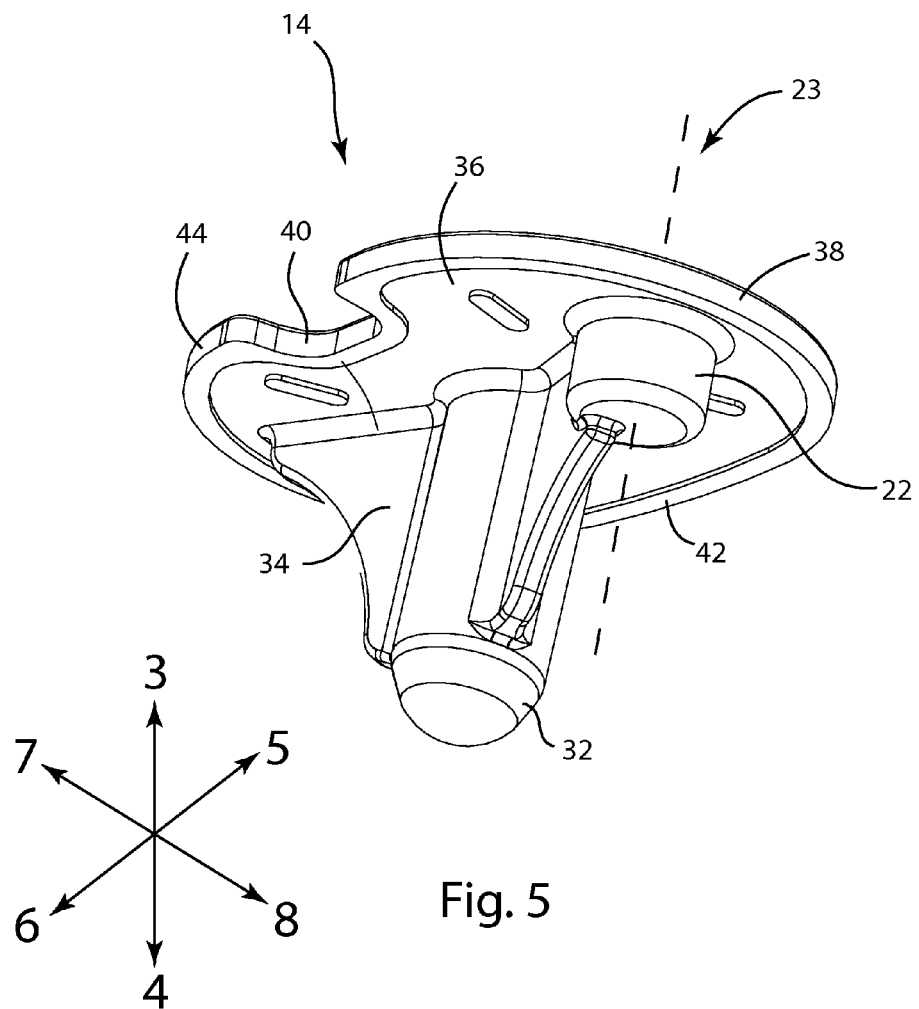
FIG. 5 illustrates a perspective bottom view of the tibial baseplate of FIG. 4 with the at least one wing, the keel, the tibial baseplate aperture and the tibial baseplate cam post aperture.

Referring to FIGS. 4 and 5, the tibial baseplate 14 may be made of a cobalt-chromium alloy. Other metals, such as titanium alloys or other composites may be used as well as polymer, ceramic, or other composite materials. In this embodiment the tibial baseplate 14 is rigidly attached to the resected tibia 2 on a tibia facing surface 36. The tibia facing surface 36 may face inferiorly and may comprise a broad platform to engage the resected tibia 2. Protruding inferiorly from the tibia facing surface is a keel 32 and at least one baseplate wing 34. The keel 32 may be driven into the core of the resected tibia 2. The at least one baseplate wing 34 is broader toward the tibia facing surface 36 and narrows toward an inferior end of the keel 32. The wing 34 extends from the tibia facing surface 36 the length of the keel 32 and is in communication with the keel 32. The wing 34 may also be driven into the resected tibia 2 for added fixation and stabilization. Attachment of the tibial baseplate 14 may also be made by using cement, force fit, bone in-growth, bone screws or other method. A superior surface 28 of the tibial baseplate 14 may be substantially flat and may extend to the ends or slightly beyond the resected tibia. The tibial baseplate 14 may act as a support for the tibial insert 16. The superior surface 28 of the tibial baseplate 14 may be polished to minimize wear between the tibial baseplate 14 and the tibial insert 16. The tibial baseplate 14 includes a hole 30, for the mounting of cam post 19, which may be positioned substantially in the geometric center of the tibial baseplate 14 and is deep enough to receive at least a portion of the cam post 19. The hole 30 may be substantially circular in cross section but may be any geometric shape that compliments the cam post 19. The tibial baseplate may also include a cavity 22 apart from the hole 30 and positioned substantially medial from the geometric center and apart from a periphery 38 of the tibial baseplate 14. The cavity 22 may provide a rotational medial axis 23 for the tibial insert 16 allowing for rotational movement of the tibial insert about that medial axis 23. In this embodiment the tibial baseplate 14 may include a periphery which runs around and bounds the superior surface 28 of the tibial baseplate 14. A notch 40 may be positioned substantially in the middle of a posterior side 44 of the superior surface 28 along the periphery 38 of the tibial insert 14. An anterior side 42 is positioned opposite the posterior side 44 along the periphery 38. The notch 40 may extend toward the anterior side 42 of the tibial baseplate but may not extend as far as the hole 30. The notch 40 may allow room for retention of the PCL or another natural ligament or tendon positioned posterior the tibial baseplate 14.

Referring to FIG. 5, a perspective view illustrates the tibia-facing side 36 of the tibial baseplate 14. The keel 32 and the at least one baseplate wing 34 may comprise porous material that encourages bone in-growth and which may include elements in those pores which advocate such in-growth further.

Figure 6:
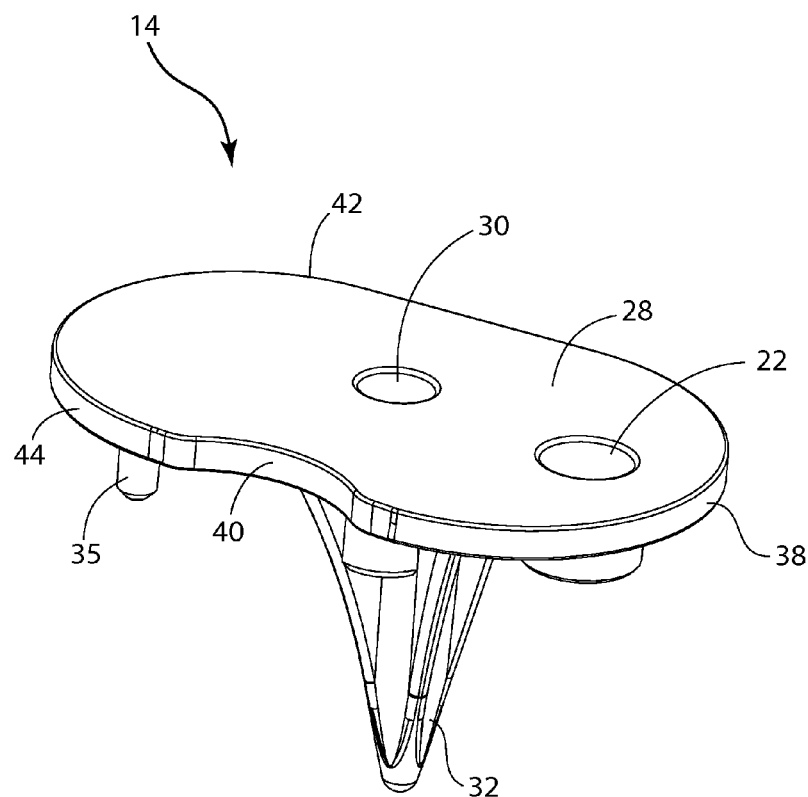
FIG. 6 illustrates a perspective top view of a different embodiment of the tibial baseplate of FIG. 1 with the tibial baseplate aperture and a tibial baseplate cam post aperture on a tibial baseplate bearing surface, a keel and at least one peg.
Figure 6:
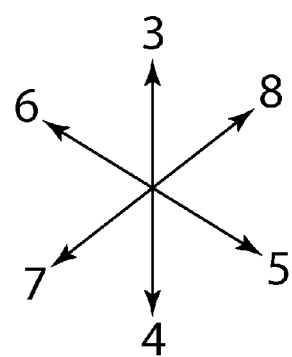
Figure 7:
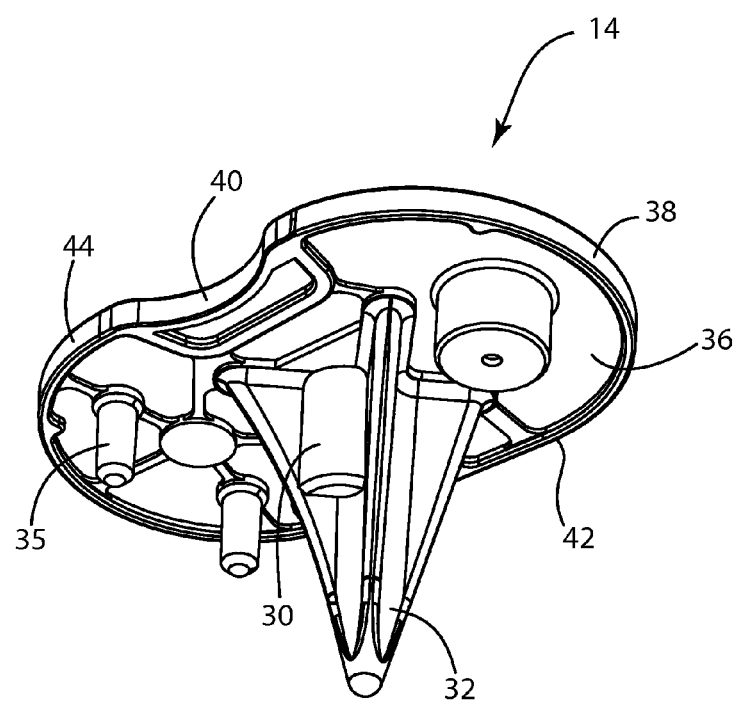
FIG. 7 illustrates a perspective bottom view of the tibial baseplate of FIG. 6 with the at least one peg, the keel, the tibial baseplate aperture and the tibial baseplate cam post aperture.
Figure 7:
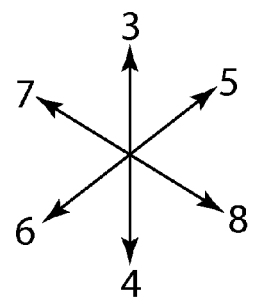

Referring to FIGS. 6 and 7, an alternate embodiment of the keel 32 is present with at least one peg 35. The peg 35 may be circular but can be any geometric shape. The peg 35 may extend inferiorly from the tibia facing surface 36 and may be smaller than the size of the keel 32. The peg 35 may also be spaced apart from the keel 32. In this and other embodiments of the device the size, shape and placement of the keel 32 may vary. The pegs 35 may not be present at all. Likewise, the tibial baseplate notch 40 can vary in size, shape and placement as well. Similar to the previous embodiment described supra, the keel 32 and at least one peg 35 may comprise porous material that encourages bone in-growth and which may include elements in those pores which advocate such in-growth further.

Figure 8:
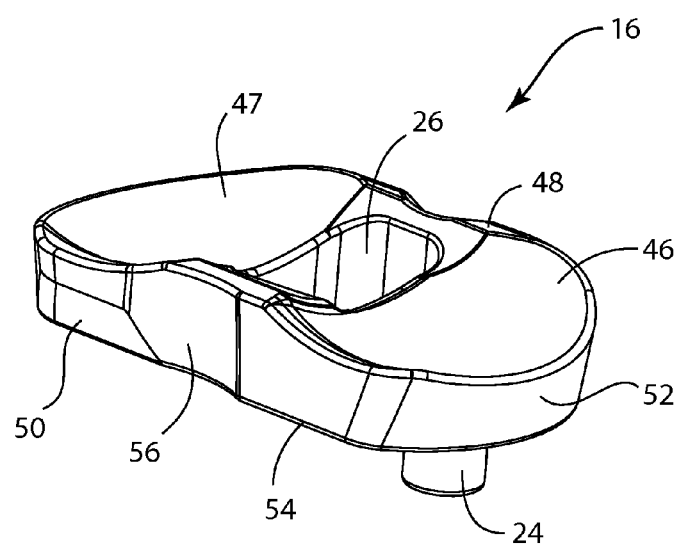
FIG. 8 illustrates a perspective top view of the tibial insert of FIG. 1 with articulating surfaces, a tibial insert notch on the posterior side to allow retention of PCL, a boss and a tibial insert channel.
Figure 8:
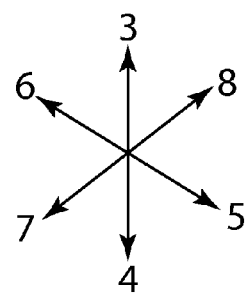

Referring to FIG. 8, the tibial insert 16 comprises a tibial baseplate facing side 54, a femoral implant facing side 55, a tibial insert periphery 52 extending around the tibial insert 16 and a tibial insert channel 26. The tibial insert periphery 52 comprises an anterior facing portion 48 and a posterior facing portion 50. The tibial insert periphery 52 bounds the tibial baseplate facing side 54 and the femoral implant facing side 55. The tibial insert channel 26 may be arc-like shaped and may be centrally located extending from the femoral implant facing side 55 to the tibial baseplate facing side 54. The tibial insert channel may be shaped to slidably fit over the cam post 19. The tibial channel 26 is large enough and shaped to allow some arc-like rotation of the tibial insert 16 after being positioned over the cam post 19. The femoral implant facing side 55 may comprise a first articulating surface 46 and a second articulating surface 47 positioned opposite the tibial insert channel 26. The first articulating surface 46 may be positioned substantially medial to the insert channel 26 and extend from the insert channel 26 to the tibial insert periphery 52. The second articulating surface 47 may be positioned substantially lateral to the insert channel 26 and extend to the tibial insert periphery 52. The articulating surfaces 46, 47 are shaped and curved to align with the femoral implant 12 for when the prosthesis 10 is implanted in the patient.

Figure 9:
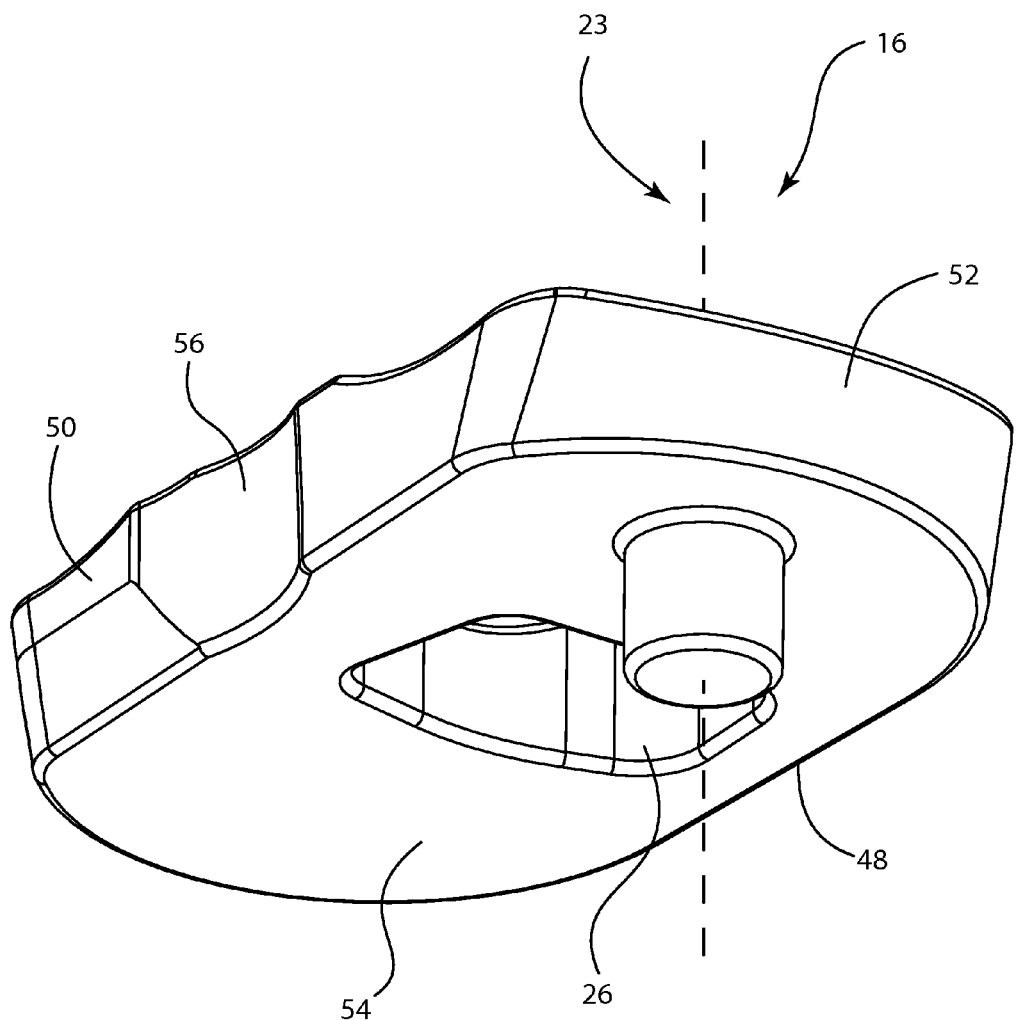
FIG. 9 illustrates a perspective bottom view of the tibial insert of FIG. 8 with the tibial insert channel, the boss, the tibial insert notch, a baseplate facing surface and an axis of rotation generally in the center of the boss.
Figure 9:
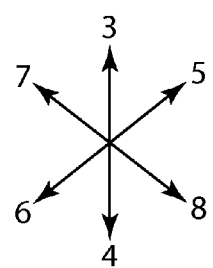

Referring to FIG. 9, the tibial baseplate facing side 54 may be substantially flat with the exception of a boss 24 extending inferiorly, positioned toward the medial side of the tibial baseplate 16 but apart from the tibial insert periphery 52. The boss 24 may be substantially circular in cross-section and fits within the complimentary cavity 22. The flat tibial baseplate facing side 54 may align with the flat superior surface 28 of the tibial baseplate 14 and the boss 24 is positioned within the cavity 22 of the tibial baseplate 14. The cavity 22 provides a rotation axis 23 of the tibial insert 16 allowing for some amount of pivot rotation about this rotation axis 23 which allows the tibial insert to perform an arc-like rotation in relation to the tibial insert channel 26 and the cam post 19. The rotation of the tibial insert 16 is constrained by the tibial insert channel 26 positioned over the cam post 19.

The tibial insert 16 can be comprised of many biocompatible materials. Polymers may be preferred but metals and ceramics may also be used.

Figure 10:
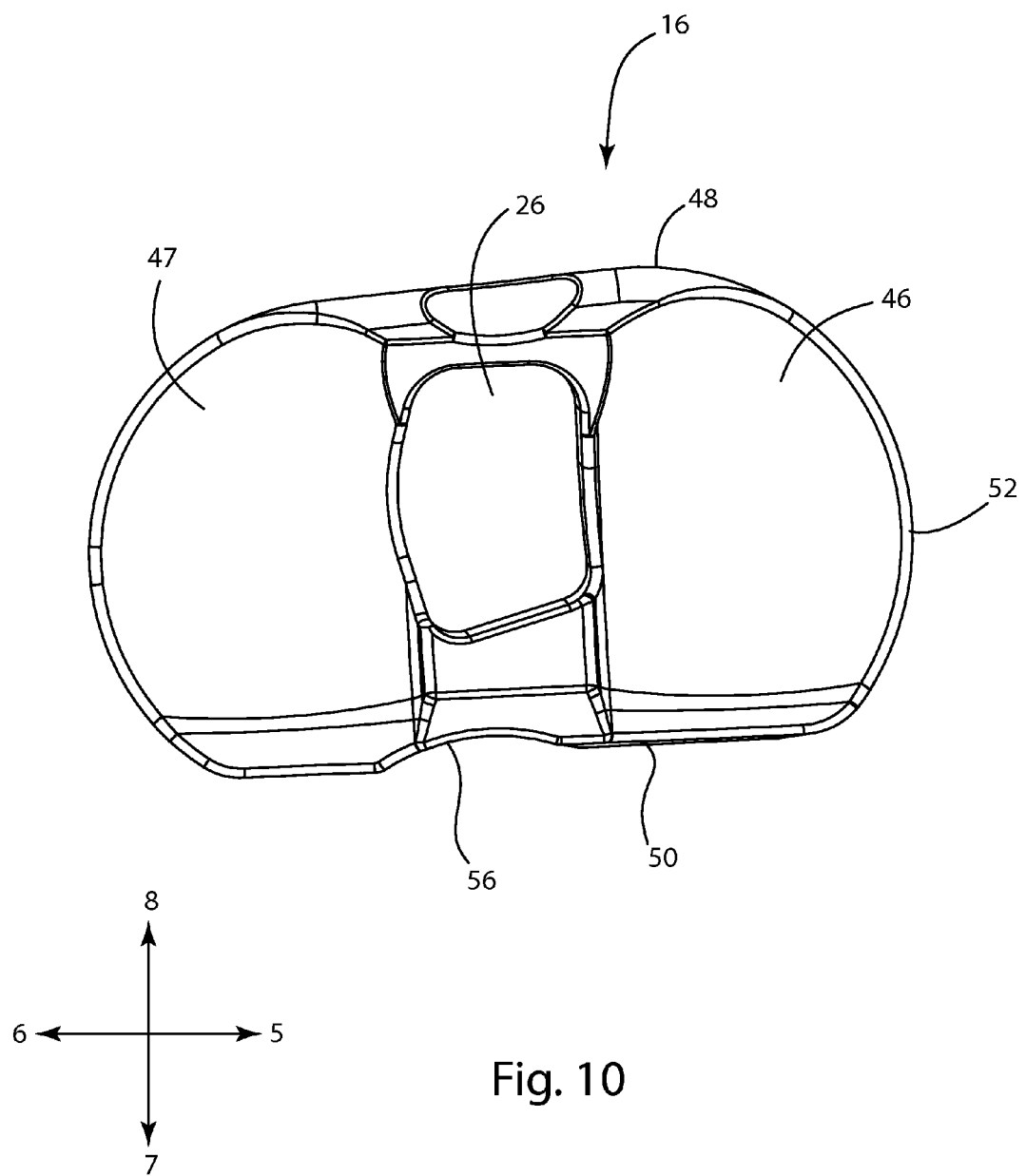
FIG. 10 illustrates a top view of the tibial insert of FIG. 8 with the articulating surfaces, the notch and the channel.

Referring to FIG. 10, a tibial insert notch 56 may be positioned along the tibial insert periphery 52 toward the posterior facing portion 50 of the tibial insert 16. The tibial insert notch 56 may extend toward the anterior facing portion 48 but not as far as the tibial insert channel 26. The tibial insert notch 56 may be aligned with the tibial baseplate notch 40 and may allow room for retention of the PCL or another ligament positioned behind the tibial baseplate 14 and the tibial insert 16.

Figure 11:
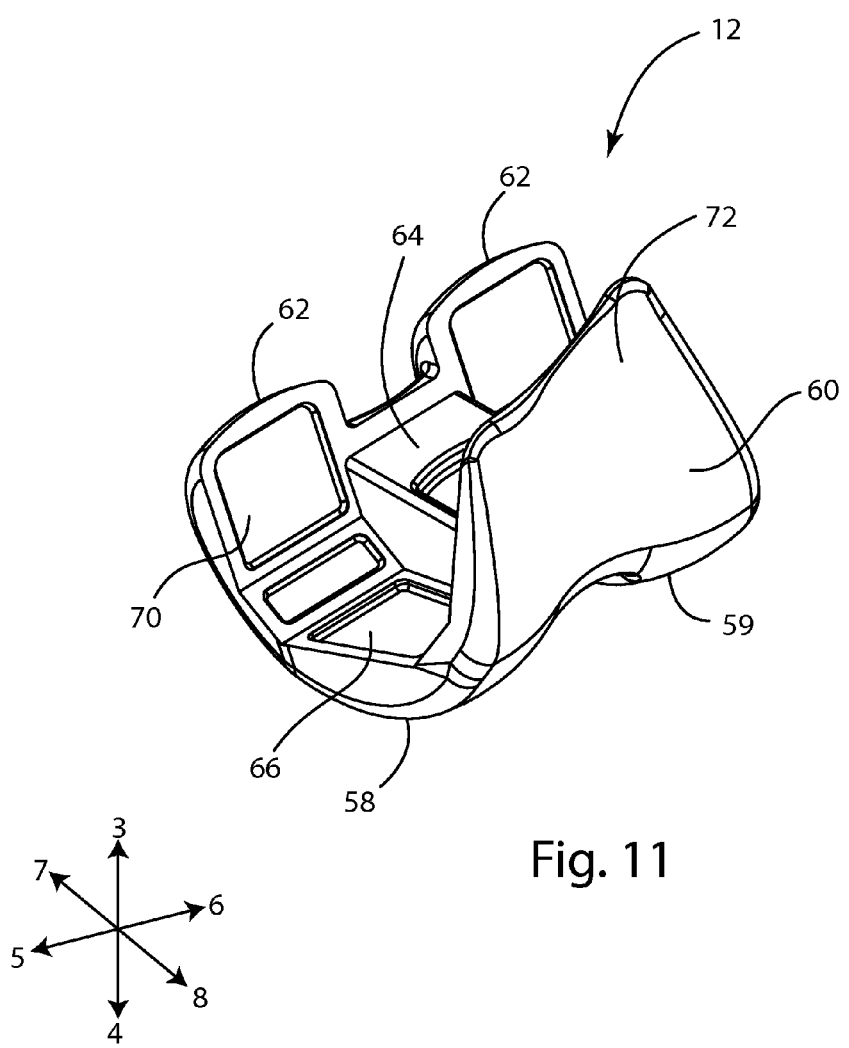
FIG. 11 illustrates a perspective front view of the femoral implant of FIG. 1 with condyles for articulation with the tibial baseplate, a cam feature for interaction with the cam post and a trochlear notch.

Referring to FIG. 11, the femoral implant 12 has a bone-facing side 70, a trochlear groove 72 on an anterior end 60 end of the femoral implant 12, and a cam feature 64. The trochlear groove 72 may be somewhat flat with a dip that extends posteriorly. The trochlear groove 72 adjoins a first condyle 58 and a second condyle 59 extending posteriorly to a posterior end 62 of the femoral implant 12. The cam feature 64 also adjoins the first and second condyles 58, 59 separate from and posterior to the trochlear groove 72. The cam feature 64 may be substantially flat on a superior and inferior side with rounded edges on each of an anterior and posterior side of the cam feature 64. The first condyle and second condyles 58, 59 may curve cephalically from the anterior end 60 to the posterior end 62, to match the contours of a natural distal end of a femur and are shaped to align with the first articulating surface 46 and the second articulating surface 47 of the tibial insert 16 respectively. The radius of curvature of the condyles 58, 59 may relatively match the same curvature of the articulating surfaces 46, 47 of the tibial insert 16. The condyles 58, 59 may be polished to minimize wear between the condyles 58, 59 and the articulating surfaces 46, 47 of the tibial insert 16. If the tibial insert 16 is also made of metal, including those metals named herein, it may also be polished to minimize wear.

The bone-facing side 70 may have a bone-facing surface 66 which may comprise a porous material to encourage bone in-growth. A gap 68 may extend between the condyles 58, 59 from the posterior end 62 and may be a fixed height, but the condyles 58, 59 may be of various widths, sizes and curvatures depending on the specific anatomy of the patient or tibial insert 16. The surface curvature of the condyles 58, 59 may also vary to match the curvature of the specific tibial insert 16 chosen for the patient's mobility requirements.

Figure 12:
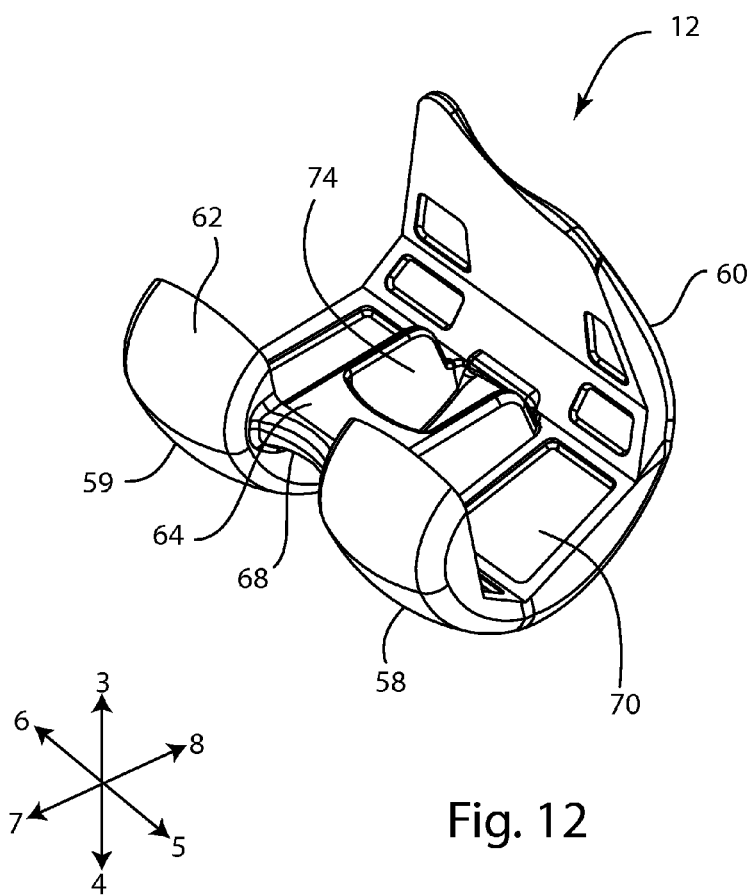
FIG. 12 illustrates a perspective back view of the femoral implant of FIG. 11 with a femoral implant opening for engagement with the cam post, a condyle gap between the condyles and condyles.

Referring to FIG. 12, the femoral implant 12 may further comprise an opening 74. The opening 74 may be bounded by the condyles 58, 59, the cam feature 64, and the trochlear groove 72. The opening 74 may be shaped and positioned to receive the cam post 19. The cam post 19 slidably inserts into the opening 74 and a posterior side of the cam post 19 engages the cam feature 64 on an anterior side of the cam feature 64 during knee flexion.

Figure 13:
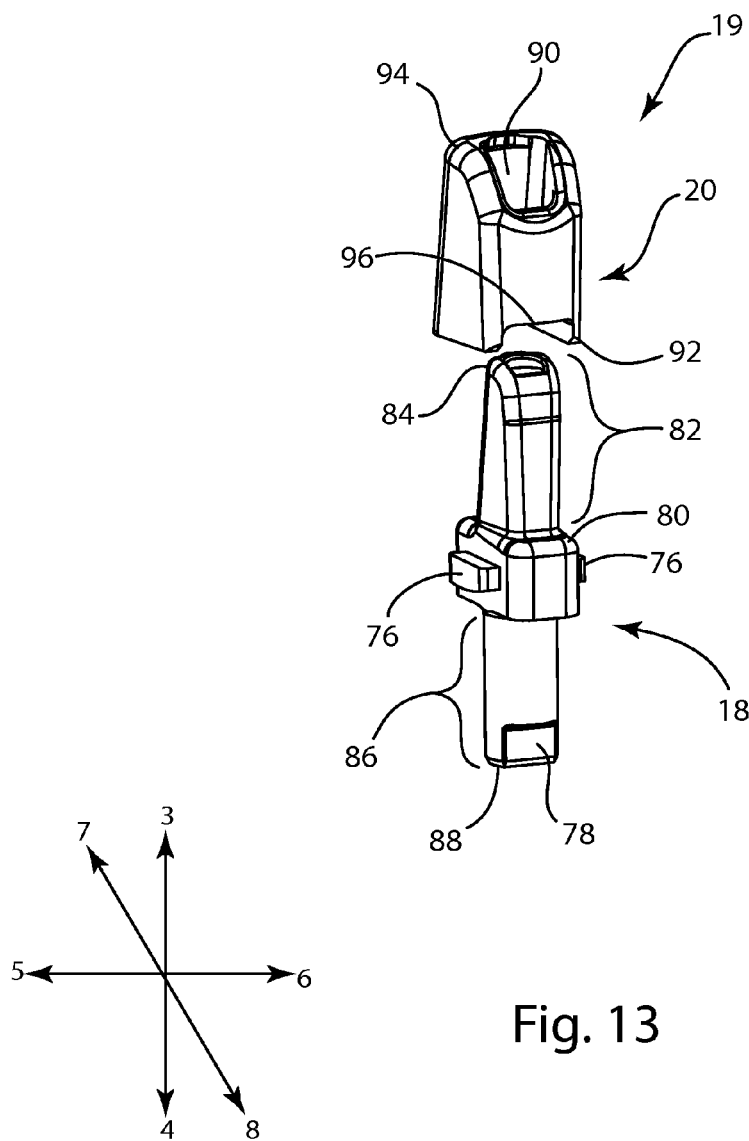
FIG. 13 illustrates an exploded perspective view of the cam post of FIG. 2 with a cam post core and an outer sleeve.

Referring to FIG. 13, the cam post 19 may comprise the cam post core 18 and the outer sleeve 20. The cam post core 18 has an inferior end 88, a superior end 84, a superior portion 82, an inferior portion 86 and an intermediate portion 80 between the superior and inferior portions 82, 86. The intermediate portion 80 may be of greater width than the inferior and superior portions 82, 86, and may comprise wings 76 extending laterally and medially and are positioned as a stop to engage the outer sleeve 20. Toward the inferior end 88 the cam post core may have a Morse taper or similar taper or pin which engages in the tibial baseplate hole 30 and a core notch 78 which may act like a key fit. The intermediate portion 80 may also vary in height (superiorly to inferiorly) depending on variations of the patients anatomy.

Figure 14:
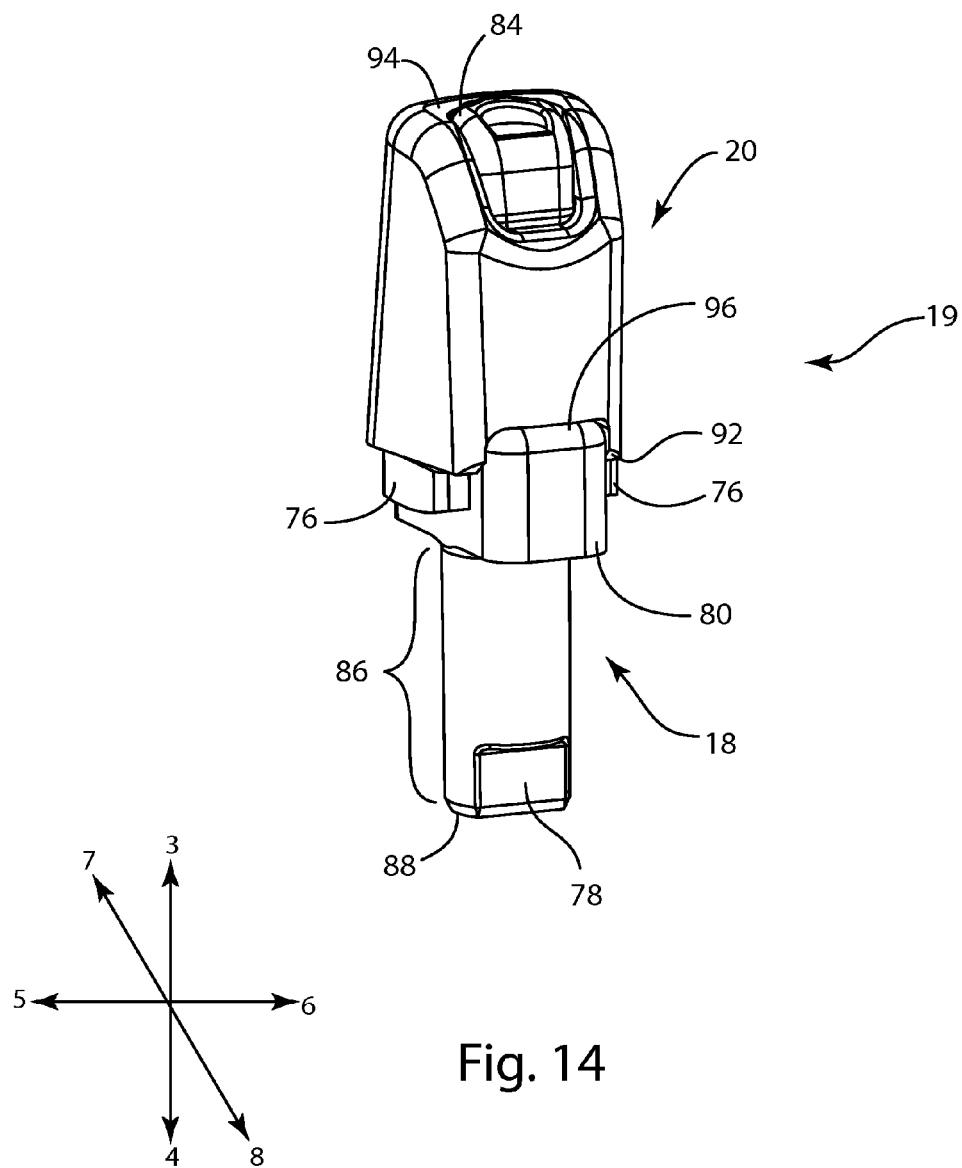
FIG. 14 illustrates the cam post of FIG. 13 with the outer sleeve at least partially encircling the cam post core.

Referring to FIGS. 13 and 14, the superior portion 82 is shaped to slidably receive the outer sleeve 20. The outer sleeve 20 has a sleeve channel 90, a superior end 94 and an inferior end 92. The sleeve channel 90 may be circular or other geometric shape which is complimentary to the shape of the superior portion 82. The sleeve channel may slide over the superior portion 82 at least partially surrounding the superior portion 82. The outer sleeve 20 is positioned around the superior portion 82 and slides onto the superior portion 82 until the sleeve inferior end 92 engages the wings 76 of the intermediate portion 80 of the cam post 19. The outer sleeve 20 may comprise a sleeve notch 96 toward the inferior end 92 of the outer sleeve 20. The sleeve notch 96 may extend superiorly and may communicate with the intermediate portion 80 and receive a portion of the intermediate portion 80 within the sleeve notch 96, providing greater stability and fixation of the cam post core 18 to the outer sleeve 20. The sleeve notch 96 may also provide rotational stops so the outer sleeve 20 is unable to rotate when snapped into engagement with the cam post core 18. The outer sleeve 20 may be secured to the cam post core 18 through snap fit features. After the outer sleeve 20 is positioned around the superior portion 82 of the cam post core 82 the cam post core superior end 84 and the outer sleeve superior end 94 may be flush.

The cam post core 18 may be made of cobalt-chrome or its alloys, titanium or its alloys, stainless steel or any other biocompatible metal, ceramic or polymer or a combination of the preceding. The outer sleeve 20 may be preferably made of polymer; however, it may also be comprised of many other biocompatible materials including ceramics and metals and combinations thereof. In addition the cam post core 18 and the sleeve 20 may be one piece instead of two pieces.

Referring back to FIG. 3, the tibial baseplate 14 is secured to the resected tibia 2. The cam post 19 may be secured to the tibial baseplate 14 using a Morse taper or similar taper or pin feature (the core notch 78 of the cam post core 18). The tibial insert 16 is positioned over the cam post 19 and the boss 24 of the tibial insert 26 is positioned within the cavity 22 of the tibial baseplate providing an axis of rotation 23. The tibial insert channel 26 may contain a metal band lining the channel 26. The sleeve 20 of the cam post 19 may be polyethylene and may extend from the sleeve superior end 94 to the tibial baseplate 14 when the cam post 19 is correctly positioned in the baseplate 14. This feature of the metal band and extension of the polyethylene sleeve 20 may minimize stresses on the tibial insert 16 when it contacts the cam post 19 and stops.

The femoral implant 12 is secured to the resected femur 1. The cam post is then positioned within the opening 74 of the femoral implant 12 engaging the cam feature 64 during knee flexion. The cam feature 64 provides rollback and femoral external rotation during knee flexion. The cam post 19 after engaging the cam feature 64 allows two fully guided rotational axes and provides anterior and posterior stabilization features. The cam post 19 engages the cam feature 64 resisting posterior tibial translation. The cam post 19 also engages the tibial insert channel 26 to restrict anterior displacement of the tibial insert 16 and the tibia as well.

One fully guided rotational axis is between the femoral implant 12 and the tibial insert 16 by engagement of the condyles 58, 59 with the articulating surfaces 46, 47. A second fully guided rotational axis is between the tibial insert 16 and the tibial baseplate 14 by aligning the tibial baseplate facing side 54 with the flat superior surface 28 of the tibial baseplate 14. The second rotational axis is accomplished by the positioning of the boss 24 within the cavity 22. The first and second rotational axes closely match the motion of the natural knee and are suitable for hard-on-hard bearing contact surfaces, such as the use of cobalt-chrome, ceramic, composite or other hard materials for the femoral implant 12, tibial insert 16 and tibial baseplate 14, which may lead to longer durability of the prosthetic knee. The potential advantage of using exclusively hard materials is that polyethylene debris can be eliminated and wear particle generation can be reduced, reducing the chance of osteolysis and implant loosening. However, to be able to use exclusively hard materials requires a fully guided motion conforming mobile bearing design—meaning a design in which relative motion between any two parts occurs along only one path.

Cobalt-chrome and its alloys are not the only hard-on-hard material that may be used, other examples include, but are not limited to, stainless-steel, titanium and its alloys, titanium carbide, titanium nitride, ion-implantation of titanium, diffusion hardened metals, diamond like coatings, diamond-like carbon, zirconium nitride, niobium, oxinium or oxidized zirconium, ceramics such as alumina and zirconia, and many other biocompatible materials and coatings.

Another advantage of the features recited herein is that this design provides knee motion during flexion closer to the natural knee. Two other benefits of these novel features is that (1) the cam post 19 can provide both anterior and posterior rotational stops for the tibial insert 16, and (2) the cam post 19 can independently provide anterior and posterior translation stops for the femoral implant 12. These benefits of the design contribute to the overall stability of the prosthetic knee, eliminate the risk of bearing spin out, and limit anterior tibial translation which is provided by the anterior cruciate ligament in the normal knee.

In alternative embodiments, the various components shown and described herein may have different sizes, configurations (such as size of the keel, shape and size of the cam post, the width of tibial insert, and the like) material properties, and other variations to adapt them to variations in patient anatomy. If desired, multiple versions of each of the femoral implant, tibial baseplate, and tibial insert components may be provided together in a single kit to enable a surgeon to interoperatively select the best set of components for a patient.

Figure 15:
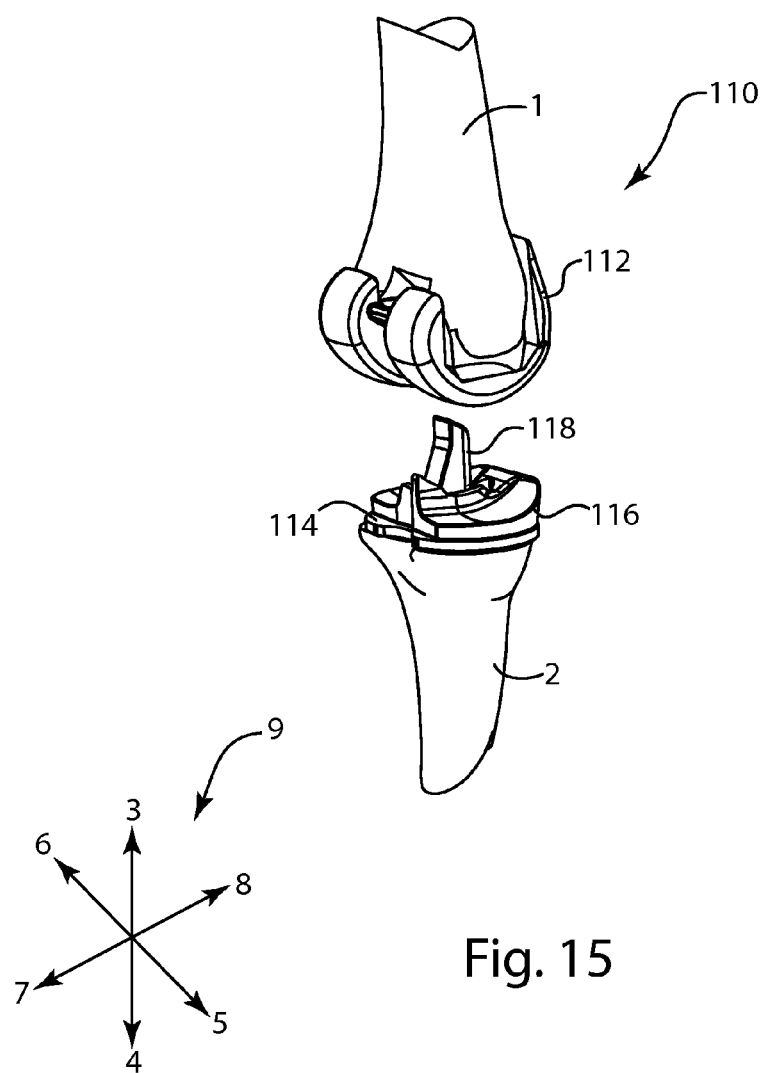
FIG. 15 illustrates a perspective view of an alternate embodiment of the prosthesis with a femur, a tibia, femoral implant, a cam post a tibial insert and a tibial baseplate.

Referring to FIG. 15, an alternate embodiment of a prosthesis 110 includes a, a femoral implant 112, a tibial baseplate 114, a tibial insert 116 and a cam post 118. The interaction between each of the components is similar to the previous embodiment.

Figure 16:
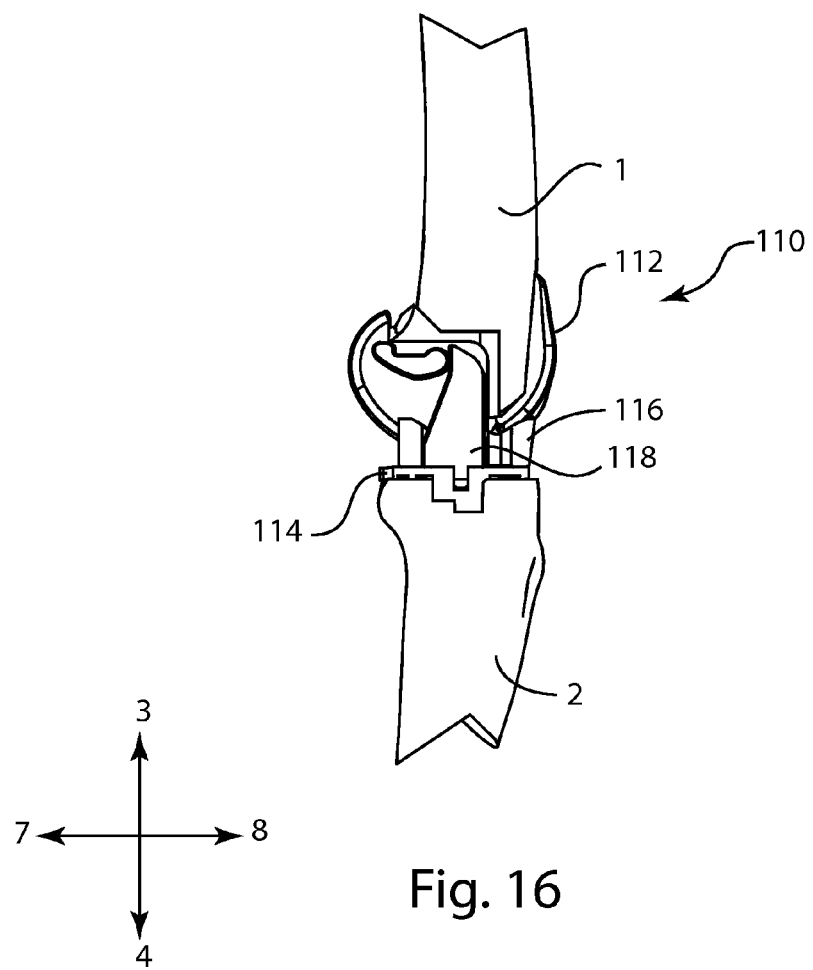
FIG. 16 illustrates a cross sectional side view of the prosthesis of FIG. 15 with the femoral implant the cam post, the tibial insert and the tibial baseplate.

Referring to FIG. 16, similar to the previous embodiment the femoral implant 112 engages the tibial insert 116 and the cam post 118 may engage a cam feature 120 during flexion of the knee providing anterior and posterior translational stops for the femoral implant. The cam post 118 is fixed to the tibial baseplate 114 and passes through a tibial insert channel 130 (better depicted in FIGS. 19 and 20). The cam post 118 provides anterior and posterior rotational stops for the tibial insert 116.

Figure 17:
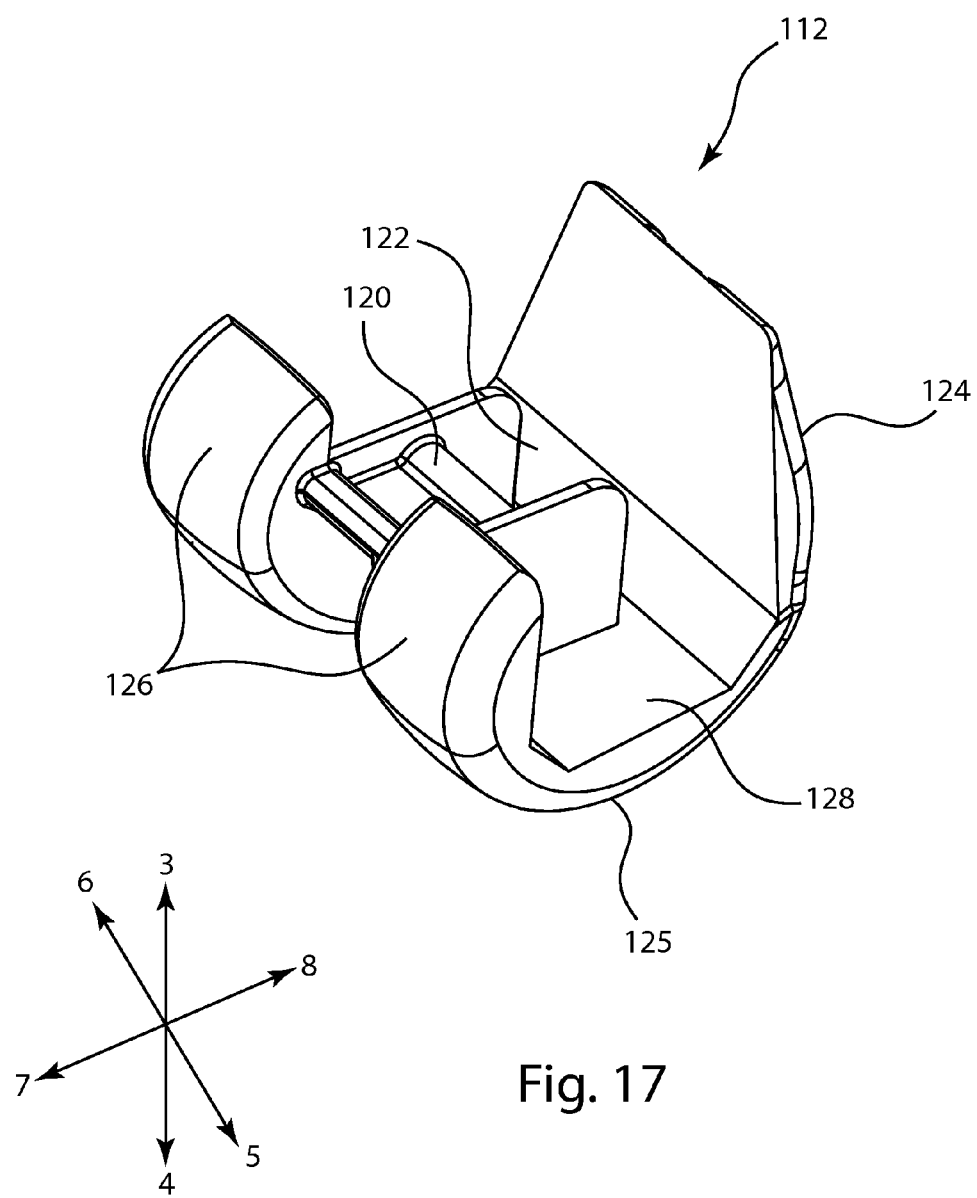
FIG. 17 illustrates a perspective back view of the femoral implant of FIG. 15 with a cam feature, condyles, and a femoral opening.

Referring to FIG. 17, the femoral implant 112 includes condyles 125 which interact with and are highly conforming with the tibial insert 116. The femoral implant also includes a bone facing side 128 that is configured to engage a resected femur. Between an anterior end 124 and a posterior end 126 lies a femoral implant opening 122 shaped to receive the cam post 118 and immediately posterior to the opening 122 is a cam feature 120 which is positioned and shaped to engage the cam post 118 during flexion of the prosthesis 110. The cam feature 120 provides rollback and femoral external rotation during knee flexion.

Figure 18:
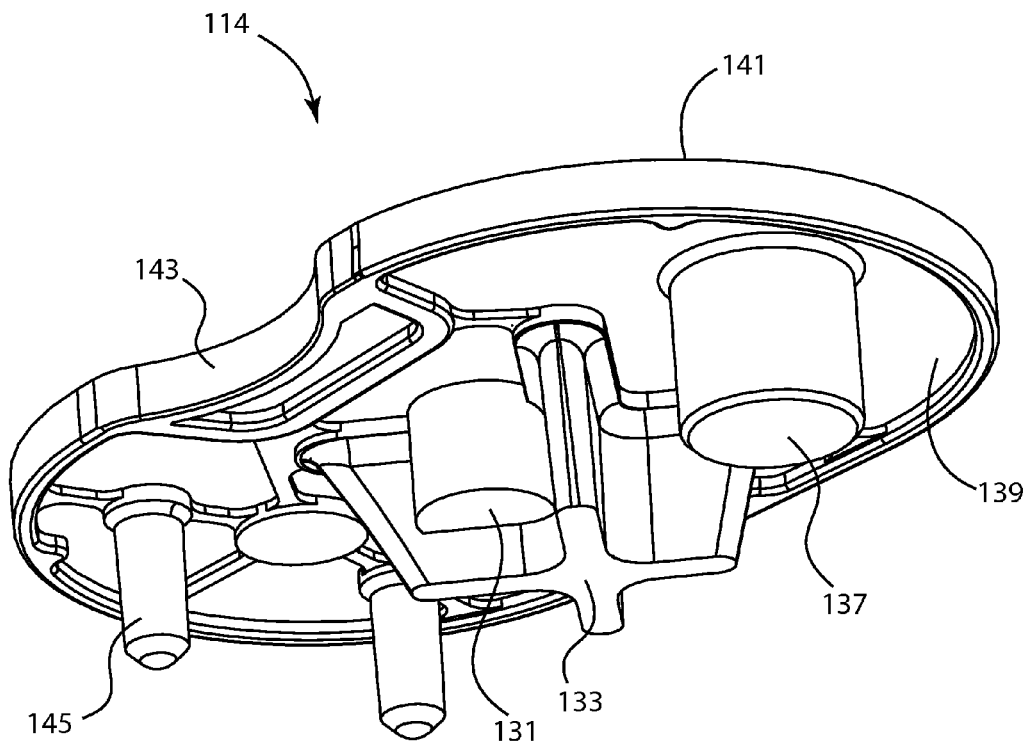
FIG. 18 illustrates a perspective bottom view of the tibial baseplate of FIG. 15 with a keel (smaller than the keels of FIGS. 4-7), at least one peg, a cavity to receive a boss of the tibial insert and tibial facing side and a notch on the posterior side for retention of the PCL.
Figure 18:
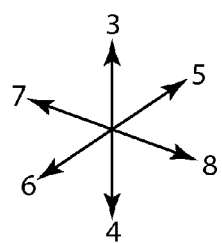

Referring to FIG. 18, the tibial baseplate 114 is similarly shaped to the previous embodiment's baseplate 14. However, a keel 133 may be shorter. The tibial baseplate 114 may comprise the same elements of the previous embodiment and they may carry out the same functions of the previous embodiment as well. The parts of the tibial baseplate which may mirror the previous embodiment include a tibial baseplate hole 131 to engage the cam post 18, a tibial baseplate cavity 137 to engage a boss 132 (depicted in FIG. 19), and a tibia facing surface 137 configured to engage the resected tibia 2. The features may also include at least one peg 145 extending from the tibia facing surface 137 to engage the tibia 2. A tibial baseplate superior surface 141 may be flat allowing for interaction with the tibial insert 116 similar to the previous embodiment. The tibial baseplate may also further comprise the tibial baseplate notch 143 which may allow room for retention of the PCL or another ligament posterior to the tibial baseplate 114 and the tibial insert 116.

Figure 19:
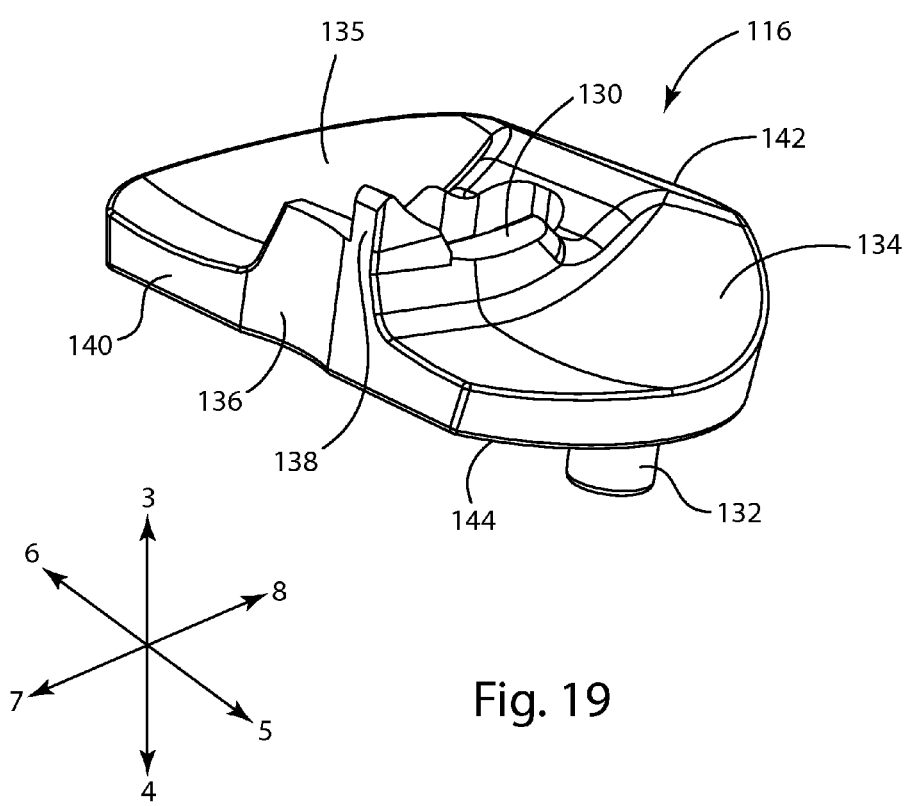
FIG. 19 illustrates a perspective top view of the tibial insert of FIG. 15 with articulating surfaces to interact with the condyles of the femoral implant of FIG. 17, a boss to interact with the cavity of the tibial baseplate of FIG. 18, a medial peak, a tibial insert channel for passage of the cam post, and a notch on the posterior side of the tibial insert for retention of the PCL.
Figure 20:
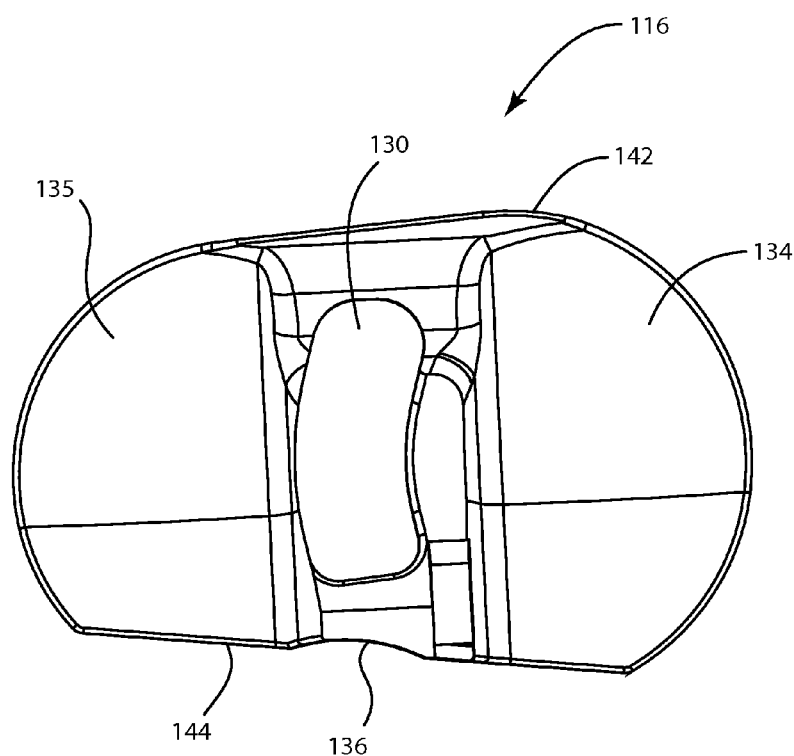
FIG. 20 illustrates a top view of the tibial insert of FIG. 19 with a channel, a notch and articulating surfaces.
Figure 20:
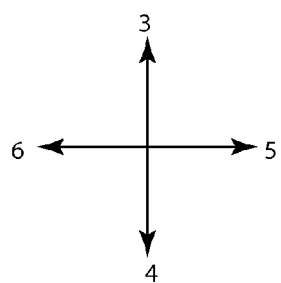

Referring to FIGS. 19 and 20, the tibial insert 116 may comprise many of the same elements with the same function and design as the previous embodiment. However, an anterior end 142 may have a greater height than a posterior end 140 of the tibial insert 116. In addition a peak 138 may extend superiorly and may be positioned toward the posterior end 140 of the tibial insert 116 to interact between, and are highly conforming with, the condyles 125 of the femoral implant 112. The other characteristics of the tibial insert 116 include a medial and a lateral articulating surfaces 134, 135 sculpted and curved to align with the condyles 125 of the femoral implant, as well as the tibial insert channel 130 which may be somewhat arc shaped (Refer to FIG. 17), which is large enough to slidably receive the cam post 118 and allows for anterior posterior rotation along the arced channel 130. Furthermore the tibial insert 116 includes the tibial insert baseplate facing surface 144 which may be flat configured to align with the flat tibial baseplate superior surface 144, and the boss 132 shaped to align and be received within the cavity 137 to provide a rotational axis for the anterior posterior rotation of the tibial insert 116. The tibial insert 116 also includes the tibial insert notch 136 which may allow room for retention of the PCL or another ligament posterior to the tibial baseplate 114 and the tibial insert 116.

Figure 21:
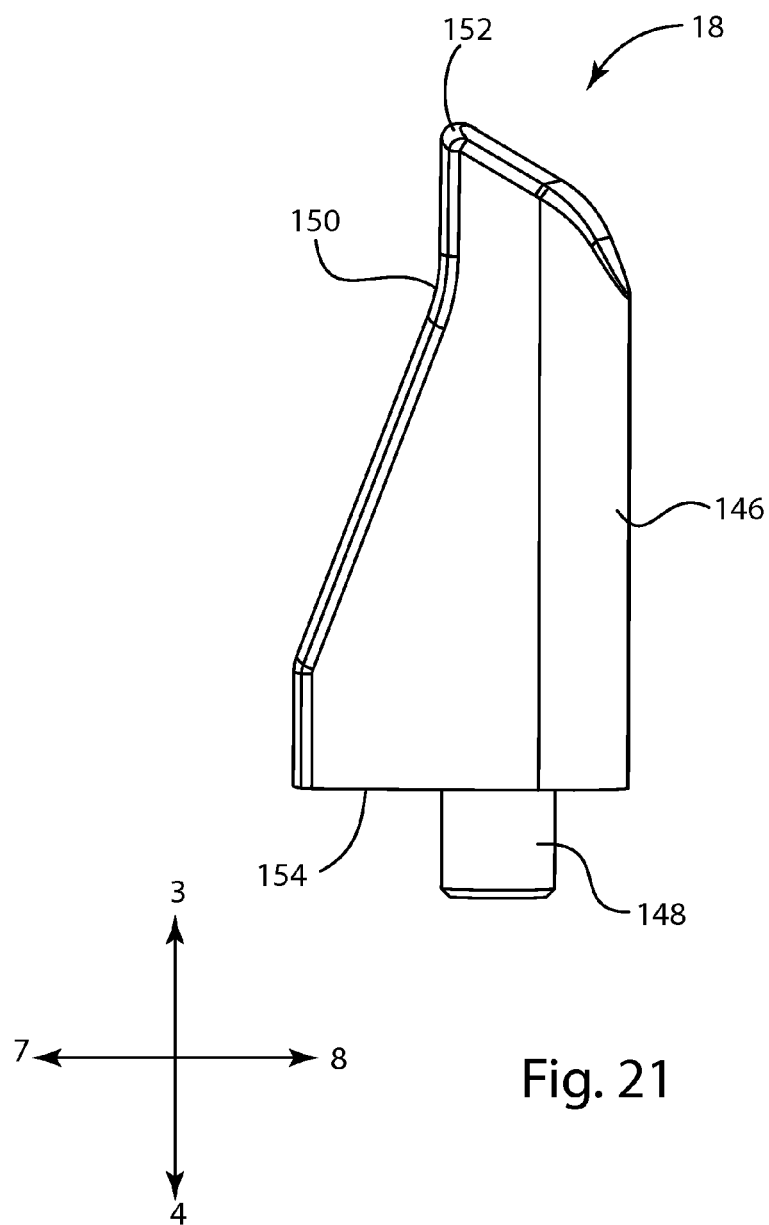
FIG. 21 illustrates a side view of the cam post of FIG. 15 with a cam post body superior end and an inferior end with a groove between the superior and inferior ends and a cam post boss extending inferiorly from the inferior end of the cam post.
Figure 22:
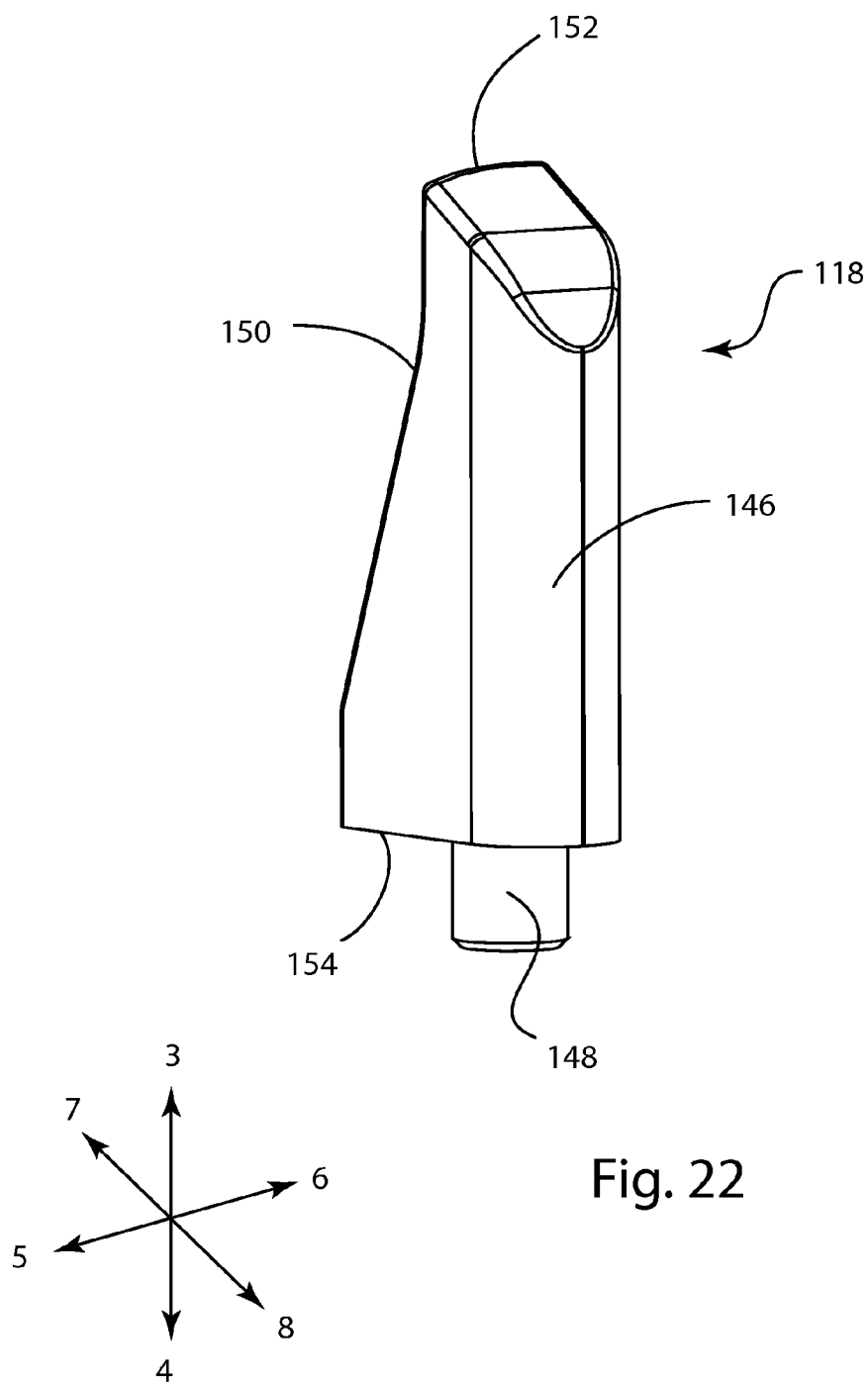
FIG. 22 illustrates a perspective front view of the cam post of FIG. 21.

Referring to FIGS. 21 and 22, the cam post 118 includes a cam post body 146 with a wider inferior end 154 than a superior end 152 and a cam post boss 148 extending inferior shaped to engage the tibial baseplate hole 131. The cam post 118 is fixed to the tibial baseplate 114 through the interaction between the tibial baseplate hole 131 and the cam post boss 148.

The cam post 118 decreases in width from the inferior end 154 to the superior end 152. Between the superior end 152 and the inferior end 154 is a groove 150 passing from a medial to lateral direction on the posterior side of the cam post 118. The groove 150 is shaped to engage the cam feature 120 of the femoral implant 112 during flexion of the prosthesis 110. An anterior side of the cam post 118 may sloop gradually from the superior end 152. The gradual sloop may allow for easier flexion and extension of the prosthesis when the cam post 118 is engaged with the cam feature.

The interaction of each the components may be similar to the previous embodiment with differences in structure only (refer to FIG. 13). The features recited herein are that this design provides knee motion during flexion closer to the natural knee. Benefits of these features include the same features as previously recited which are (1) the cam post 118 can provide both anterior and posterior rotational stops for the tibial insert 116, and (2) the cam post 118 can independently provide anterior and posterior translation stops for the femoral implant 112. These benefits of the design contribute to the overall stability of the prosthesis 110.

Figure 23:
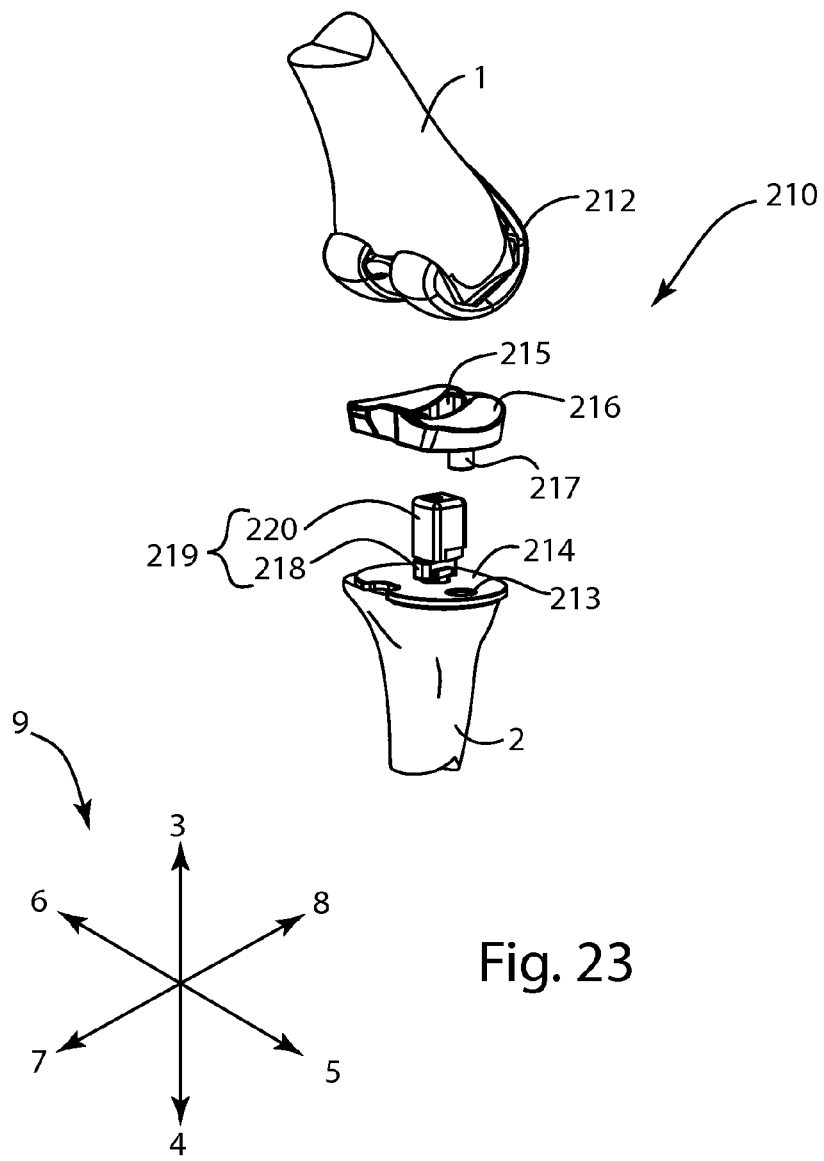
FIG. 23 illustrates an exploded perspective back view of an alternate embodiment of the prosthesis of FIG. 1 with a femur, a tibia, femoral implant, a cam post, a tibial insert and a tibial baseplate.
Figure 24:
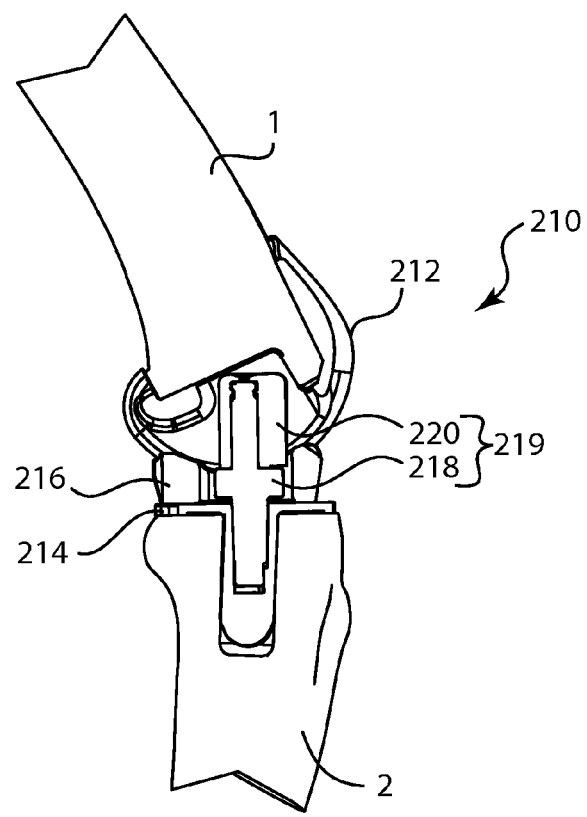
FIG. 24 illustrates a cross sectional side view of the prosthesis of FIG. 23 with a femoral implant, a cam post, a tibial insert and a tibial baseplate.
Figure 24:
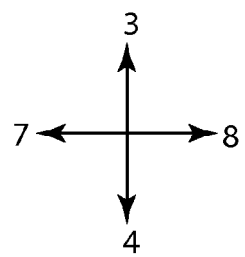

Referring to FIGS. 23 and 24, another alternate embodiment of a prosthesis 210 includes the same or similar components of the previous embodiments with a femoral implant 212, a tibial baseplate 214, a tibial insert 216 and a cam post 219 comprising a cam post core 218 and a sleeve 220. This specific embodiment is intended to prevent varus/valgus displacement and may be more suitable for those patients who have insufficient, lax or absent medial or lateral stabilizing ligaments. The tibial insert has a tibial insert channel 215 (similar to those channels 26 and 130 in the two previous embodiments) and a boss 217 (similar to those bosses 24 and 132 of the previous embodiments). The tibial baseplate 214 has a cavity toward the medial side 213

Figure 25:
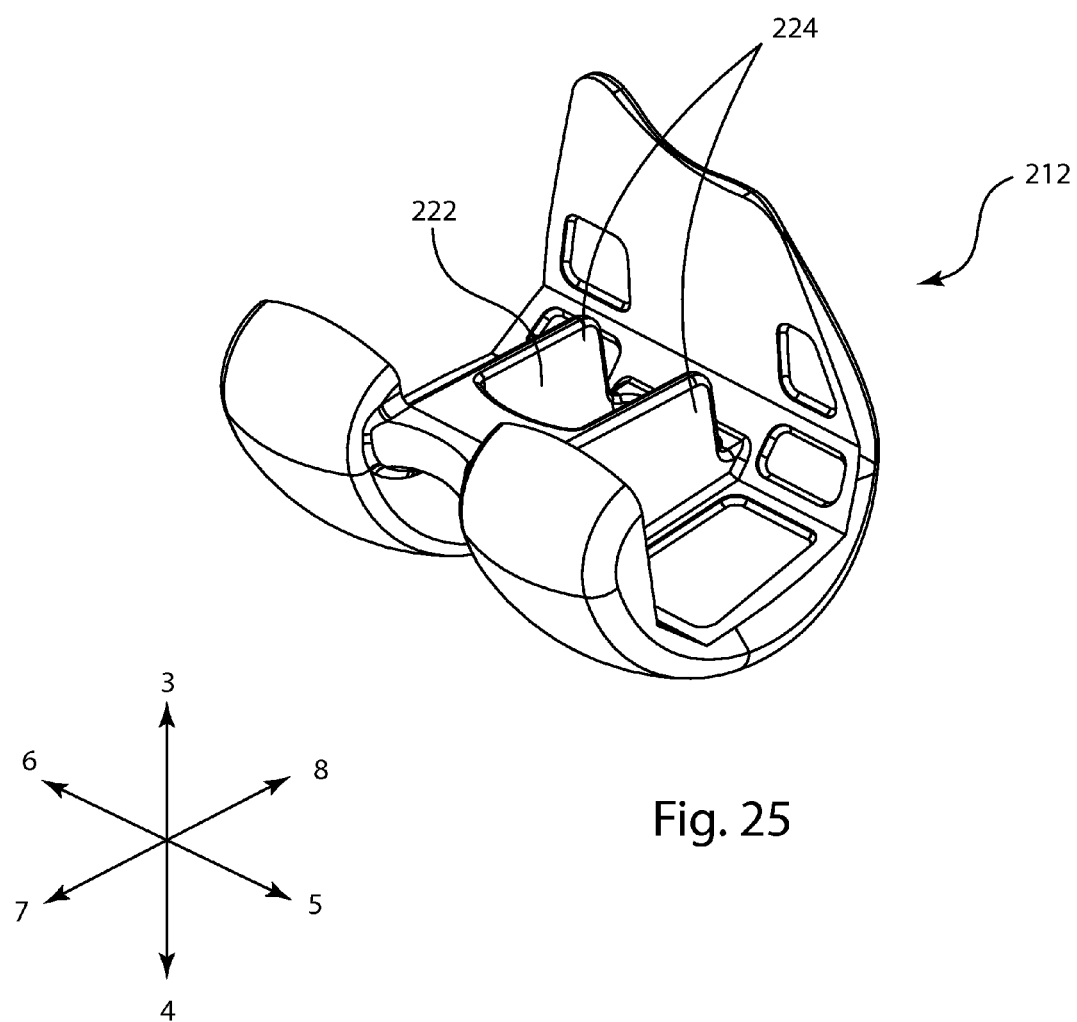
FIG. 25 illustrates a perspective back view of a femoral implant with a femoral opening engaging the cam post and opening walls for stabilization of the cam post and the prosthesis.

The components are substantially similar to the previous embodiments. The tibial insert has a tibial insert channel 215 (similar to those channels 26 and 130 in the two previous embodiments) and a boss 217 (similar to those bosses 24 and 132 of the previous embodiments). However, referring to FIG. 25, the femoral implant 212 which has a femoral opening 222 may also comprise opening walls 224. The opening walls 224 may extend in a planar fashion substantially superiorly from the bone facing surface 66 of the femoral implant 212 but not extending beyond the bounds of the posterior end 62 or the anterior end 60. The opening walls 224 may engage the cam post sleeve 220 of the cam post 219 preventing varus/valgus distraction and provide greater medial/lateral stabilization (refer to FIG. 23).

Figure 26:
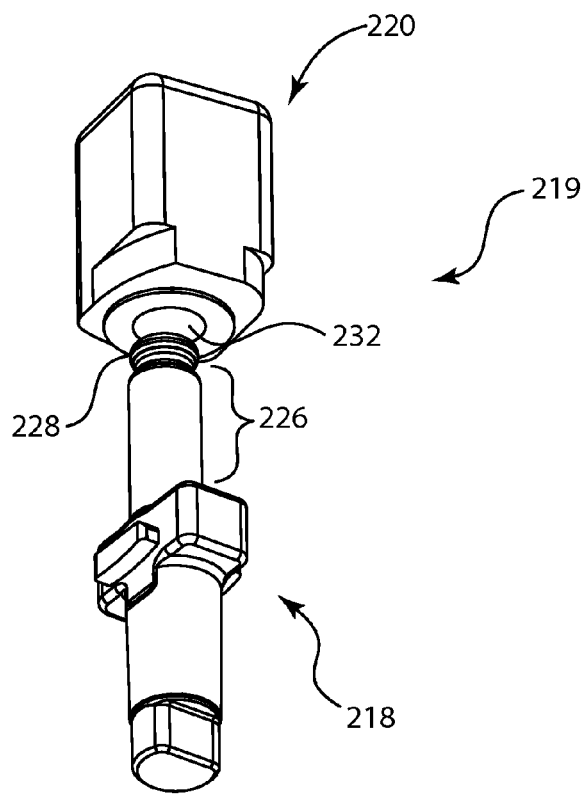
FIG. 26 illustrates a perspective view of the cam post of FIG. 23 with a cam post core with a snap feature for engaging a cam post sleeve.
Figure 26:
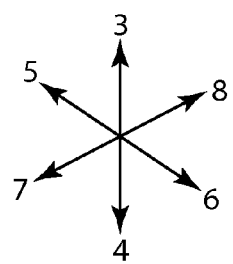

Referring to FIG. 26, the cam post core 218 comprises most of the same features of the cam post core 18 of FIGS. 13 and 14; however, a cam post core superior portion 226 may be substantially circular in cross section with a snap feature 228 on the superior end shaped to snap into engagement with the sleeve 220. The sleeve 220 may be substantially rectangular in cross section; however any shape that would enable engagement with the femoral implant 212 opening walls 224 is sufficient. The sleeve 220 has a cylindrical bore 232 passing longitudinally there through and a taper 230 toward the inferior end of the sleeve 220 to prevent any obstruction of the sleeve with the tibial insert channel 215. The cam post core superior portion 226 is at least partially inserted into the sleeve 220 until the two components snap into engagement. Other means besides a snap feature may be used for engagement of the sleeve 220 to the cam post core superior portion 226. The sleeve 220 may rotate around the center axis of cam post core 218 after the sleeve is positioned around the cam post core superior portion 226. The cam post core 218 may be polished to minimize wear between the cam post core 218 and the sleeve 220. Internal stops (not shown) may be added to prevent complete rotation of the sleeve around the center axis of the cam post core 218.

Figure 27:
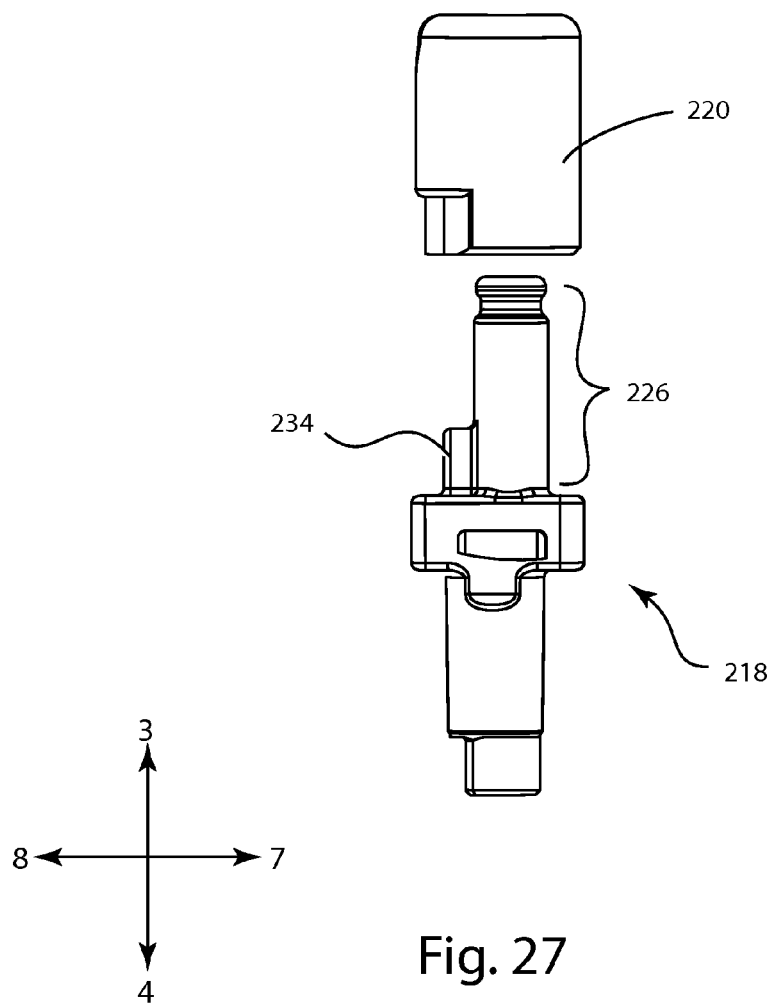
FIG. 27 illustrates a side view of an alternate embodiment of a cam post of FIG. 26 with a cam post sleeve and a cam post core the cam post core having a ridge to prevent movement of the cam post sleeve after it engages the cam post core.
Figure 28:
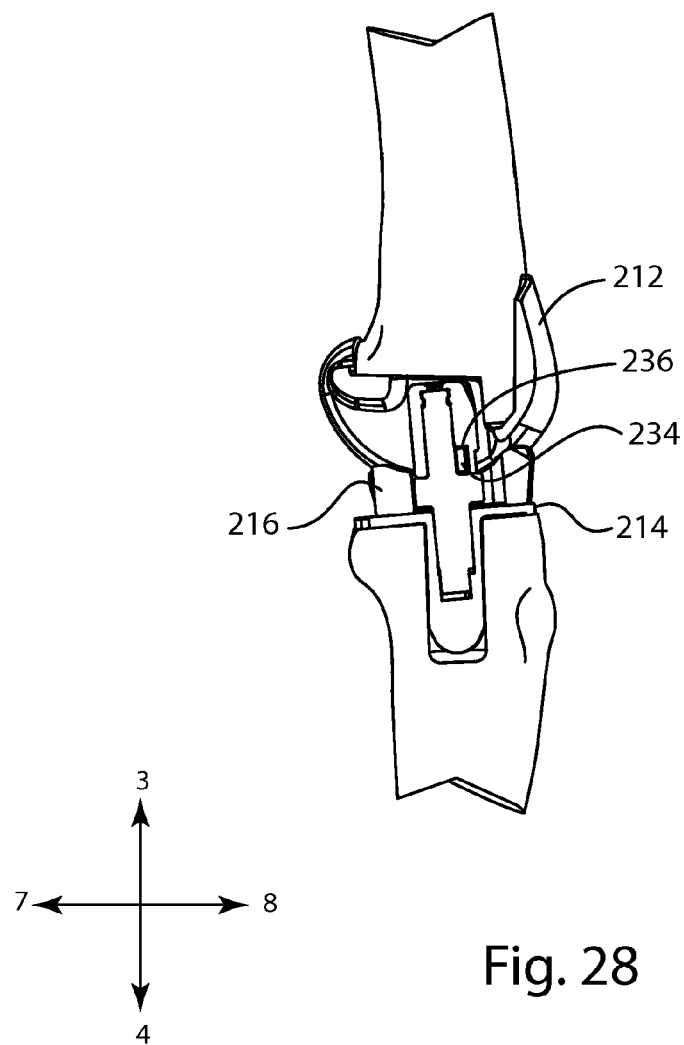
FIG. 28 illustrates slightly different embodiment of the prosthesis of FIG. 23 (the only difference is in the cam post of FIG. 26) showing the cam post of FIG. 27.

Referring to FIGS. 27 and 28, an alternate embodiment of the cam post core 218 may have a ridge 234 which may extend superiorly from an intermediate portion (similar to intermediate portion 80 of FIG. 14) and such ridge may extend either posteriorly or anteriorly from the cam post core superior portion 226 of the cam post core 218. The ridge 234 may be narrower and shorter than the cam post core 226. The sleeve 220 may provide a complimentary fit shaped bore 236 that concentrically fits the cam post core superior portion 226 with the ridge 234 of the cam post core 218. This ridge 234 prevents any rotational movement of the sleeve 220. Any other means may be used to prevent rotational movement of the sleeve 220 around the cam post core 218. Again, the cam post core 218 and the sleeve 220 may be one piece instead of two pieces.

Figure 29:
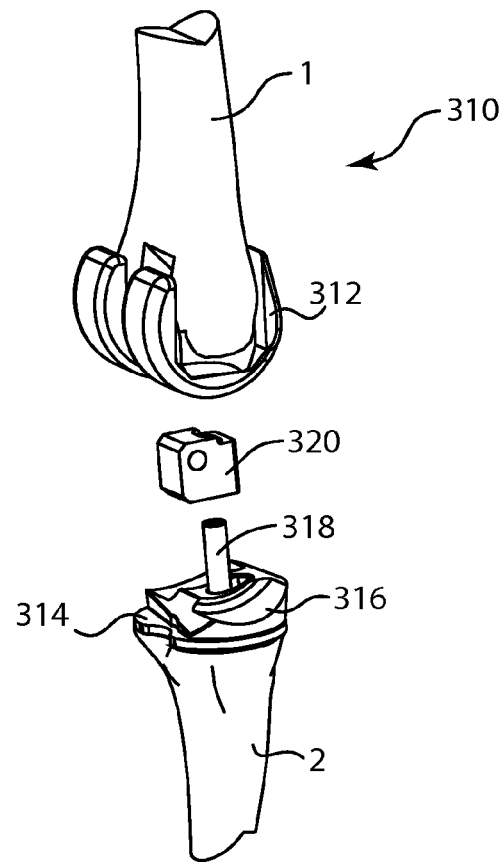
FIG. 29 illustrates an exploded perspective back view of an alternate embodiment of the prosthesis of FIG. 1 with a femur, a tibia, a femoral implant, a tibial insert, a tibial baseplate, a cam post and a hinge block which slides around the cam post.
Figure 29:
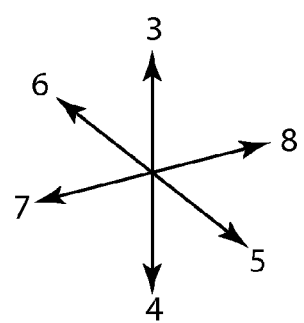
Figure 30:
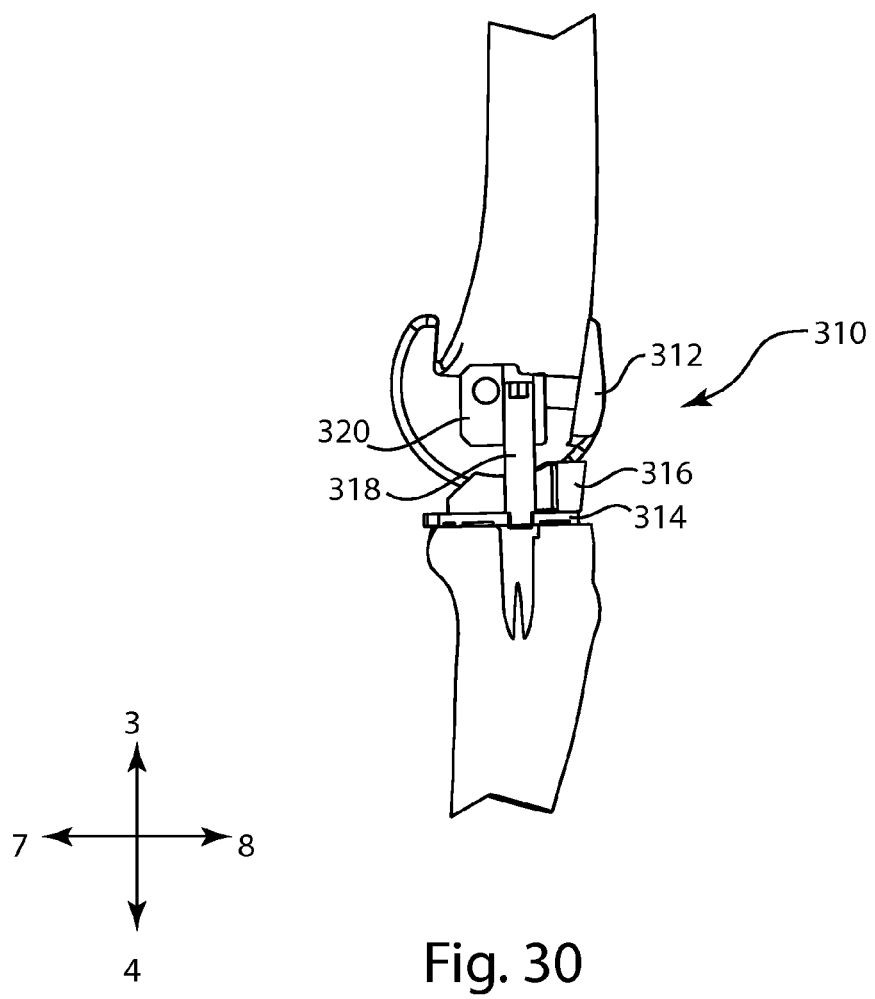
FIG. 30 illustrates a cross section side view of the prosthesis of FIG. 29 with the femoral implant secured to the femur, the femoral implant engaging the hinge block, the hinge block around the cam post, the condyles of the femoral implant articulating against the tibial insert, the tibial insert engaging the tibial baseplate and the tibial baseplate secured to the tibia.
Figure 31:
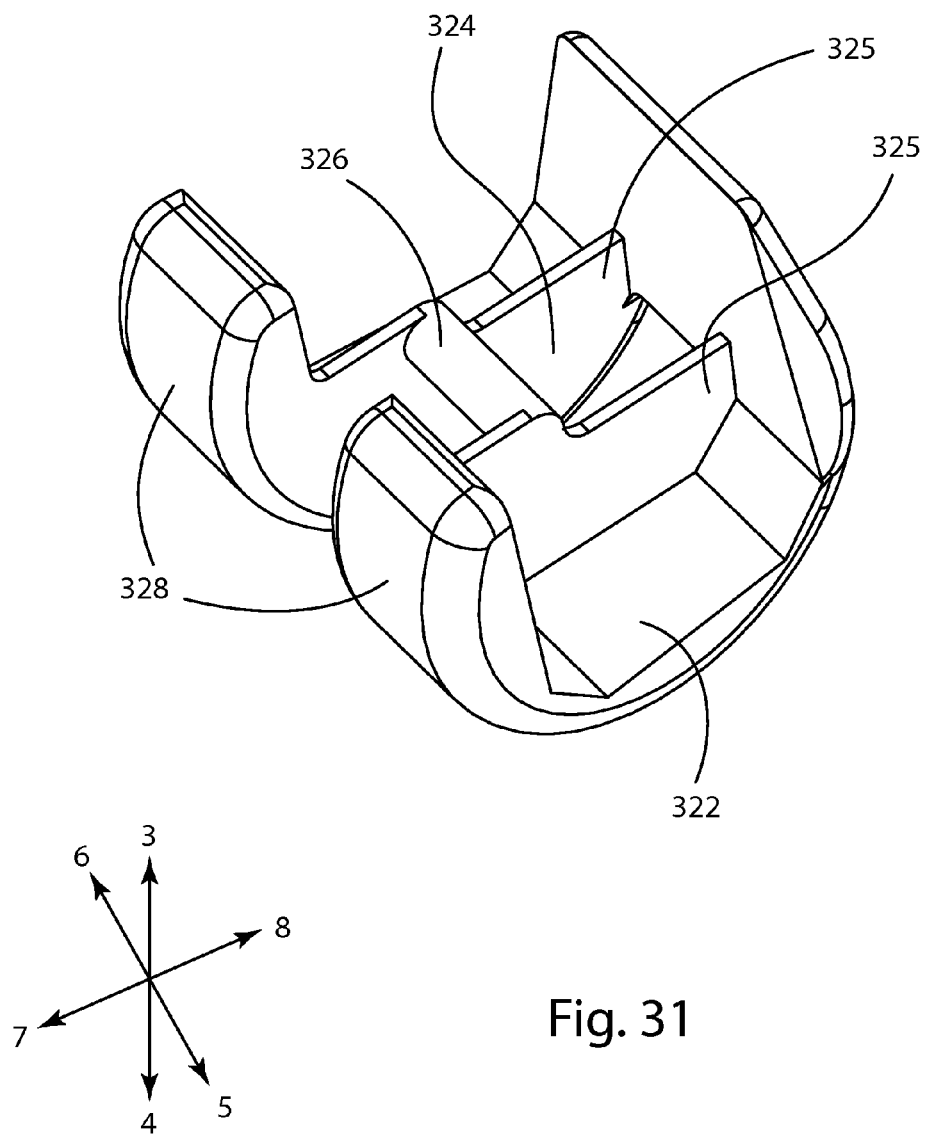
FIG. 31 illustrates a perspective back view of the femoral implant of FIG. 29 with condyles, an opening, opening walls to restrain varus/valgus movement, and an eccentric pin to pass through an opening in the hinge block to stabilize the hinge block (and the prosthesis) within the femoral implant.

Referring to FIGS. 29 and 30, a further embodiment of a prosthesis 310 includes a femoral implant 312, a tibial baseplate 314, a tibial insert 316, a cam post 318 and a hinge block 320. The tibial baseplate 314 and the tibial insert may substantially mirror any of the previous embodiments recited herein with the medial rotational axis. Referring to FIG. 31, the femoral implant 312 is similar to the previous embodiments recited herein with a femur facing side 322, a femoral implant opening 324 and condyles 328 match the curvature of the specific tibial insert 316 chosen for the patient's mobility requirements. However, the femoral implant 312 also includes an eccentric pin 326 which is insertable into the hinge block 320 and opening walls 325 (similar to the opening walls 224 of FIG. 25) which engage the hinge block and help in preventing varus/valgus displacement and axial distraction, and provide greater medial/lateral stabilization (refer to FIG. 29).

Figure 32:
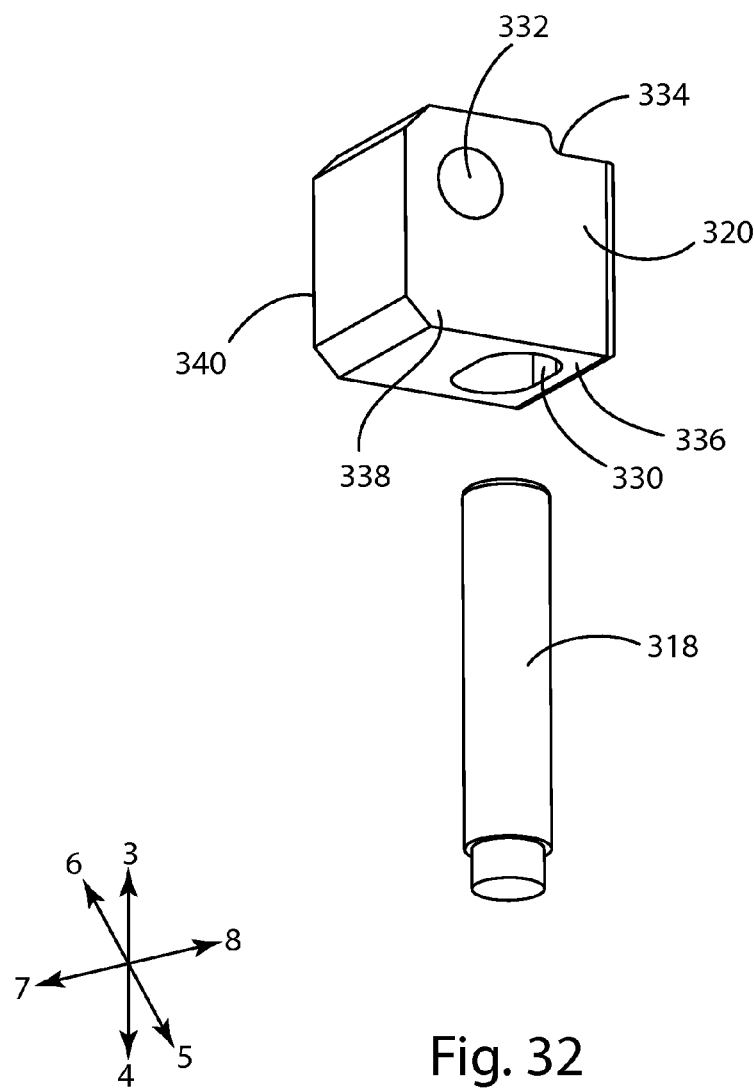
FIG. 32 illustrates a perspective view of the hinge block and cam post of FIG. 29 with the hinge block with a first bore running superiorly/inferiorly for engaging the cam post and a second bore running medial/laterally for engaging the eccentric pin of the femoral implant.
Figure 33:
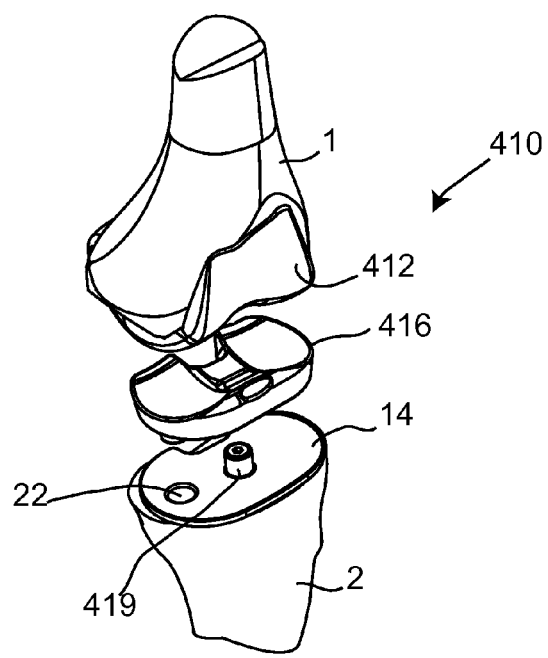
FIG. 33 illustrates a perspective view of an alternate embodiment of the prosthesis of FIG. 1 with a femur, a tibia, a femoral implant, a tibial baseplate and a tibial insert.
Figure 33:
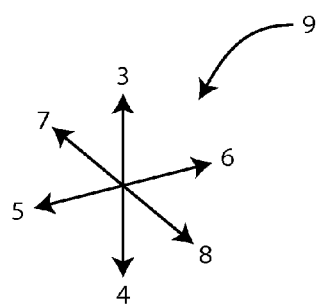

Referring to FIG. 32, the cam post 318 may be substantially circular in cross section with a Morse taper or similar taper toward the inferior end. The hinge block 320 may be substantially rectangular in cross section and may include a first bore 330 extending superiorly/inferiorly through the block from a superior end 334 to an inferior end 336. The first bore 330 is positioned toward the anterior end of the block 320 while the second bore is positioned near the posterior end and superior end 334. The first bore 330 is shaped to slidably receive the cam post 318. The hinge block may also include a second bore 332 extending laterally/medially through the block 320 from a medial end 338 to a lateral end 340. The second bore is positioned and shaped to receive the eccentric pin 326 of the femoral implant 312. The eccentric pin 326 may be tubular and complimentary fits within the second bore 332. The eccentric pin 326 may rest within a relatively central location within the femoral implant 312. The eccentric pin 326 and the opening walls 325 of the femoral implant 312 provide greater medial/lateral stabilization and prevent varus/valgus distraction as well. The two bores 330, 332 of the hinge block 320 may not intersect. This embodiment may be advantageous for those patients that have insufficient, lax or absent medial or lateral stabilizing ligaments.

One method that may be used in placing the prosthesis 10 (any of the embodiments will be similar) is to attach the femoral implant 12 and tibial baseplate 14 first to the resected femur 1 and tibia 2 respectively. The order in which either of these is done is left to the preference of the surgeon. After each of the femoral implant 12 and tibial baseplate 14 is secured a trial tibial insert (not shown) with an attached trial cam post (not shown) is positioned on the tibial baseplate to determine the correct size of post and tibial insert to provide for the patients anatomy. The trial cam post is not rigidly connected to the trial insert and can move within the trial tibial insert channel. The trial tibial insert and cam post are removed and the tibial insert 16 is attached to the tibial baseplate 14 through use of the tibial insert boss 24 and the tibial baseplate cavity 22. The knee is then placed in deep flexion to allow the cam post 19 to be passed through the tibial insert channel 26 and secured to the tibial baseplate 14 in the tibial baseplate hole 30. The knee is then extended to position the cam post 19 in the femoral implant opening 74.

While this method is specifically recited herein, other methods may also be performed such as first attaching the cam post 19 to the tibial baseplate 14 and then passing the tibial insert 16 over the cam post 19. The tibial insert 16 may then be secured to the tibial baseplate 14 and the knee extended to engage the cam post 19 with the femoral implant opening 74.

Figure 34:
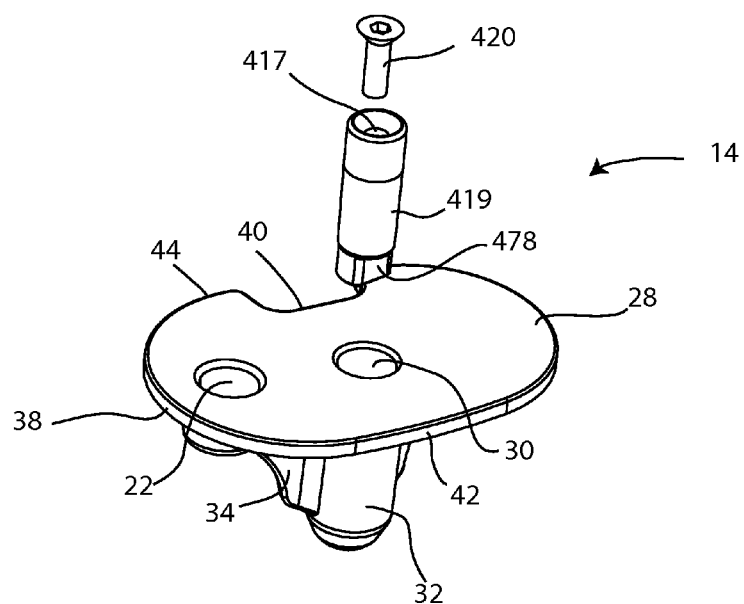
FIG. 34 illustrates an exploded perspective view of the tibial baseplate of FIG. 33 substantially similar to that of FIG. 4 with a tibial baseplate notch, a hole, a cavity, however with a different post than in FIG. 4 and with a screw.
Figure 34:
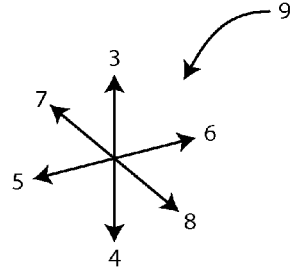
Figure 35:
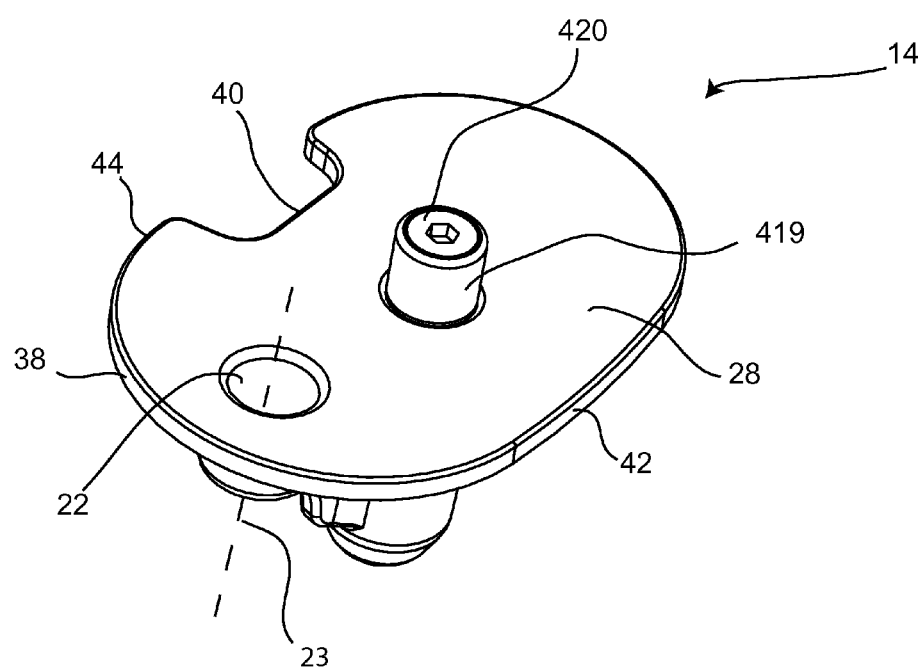
FIG. 35 illustrates a perspective view of the tibial baseplate of FIG. 34, with the post and screw engaged in the hole of the tibial baseplate.
Figure 35:
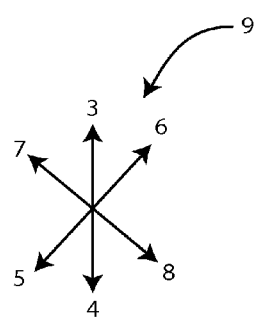

Referring to FIGS. 33-41, an alternate embodiment of a prosthesis 410 includes a femoral implant 412, a tibial insert 416, and a tibial baseplate 14. The tibial insert 416 may be similar to the tibial insert 16 previously described above. In this embodiment the tibial baseplate 14 may be made of a cobalt-chromium alloy. Other biocompatible metals (particularly a titanium alloy), polymer, ceramic, or composite materials could also be used, or the tibial baseplate may comprise two or more different materials. In this embodiment the tibial baseplate 14 is rigidly attached to the resected tibia 2 substantially similar as previously disclosed herein including, using cement, force fit, bone ingrowth, bone screws or other method. As shown in FIGS. 34 and 35, the tibial baseplate 14 includes the hole 30 for a post 419 to provide a rotational stop when mounted to the tibial insert 416 similar to the embodiments previously disclosed herein. The cavity 22 provides a rotation axis 23 for the tibial insert 416. The post 419 may comprise a tubular body with a bore 417 passing from a superior end of the body at least partially longitudinally through the center of the post. The post bore 417 may be configured to receive a screw 420. The post 419 may comprise a taper 478 or notch extending from an inferior end of the post. The taper 478 may extend into the body of the post 419 and may be configured to fit like a key into the hole 30 of the tibial baseplate 14 in a manner substantially similar as previously disclosed. The screw 420 may be substantially circular in cross-sectional shape. The screw 420 may have a body and a head wherein the body may extend inferiorly from the head. The body of the screw may have a smaller diameter than the head. The screw 420 may engage the post bore by using threads, press fit, snap fit or any other means to fixedly attach a screw to a body. The screw 420 is capable of being released after it has been attached to the post 419. In this embodiment the post bore 417, at implantation, is plugged with the screw 420 which may be made of ultra-high molecular weight polyethylene. If removal of the post 419 is necessary, a threaded removal tool may be screwed into the post bore 417. The taper 478 may work as an anti-rotation feature on the post 419, with a complimentary feature in the hole 30 of the tibial baseplate 14, to aid in removal.

Similarly as was previously described, the tibial baseplate 14 may comprise a tibial baseplate notch 40 positioned along a posterior side 44, of the periphery 38. The tibial baseplate notch 40 may allow room for retention of the PCL or another ligament posterior to the tibial baseplate 14.

Figure 36:
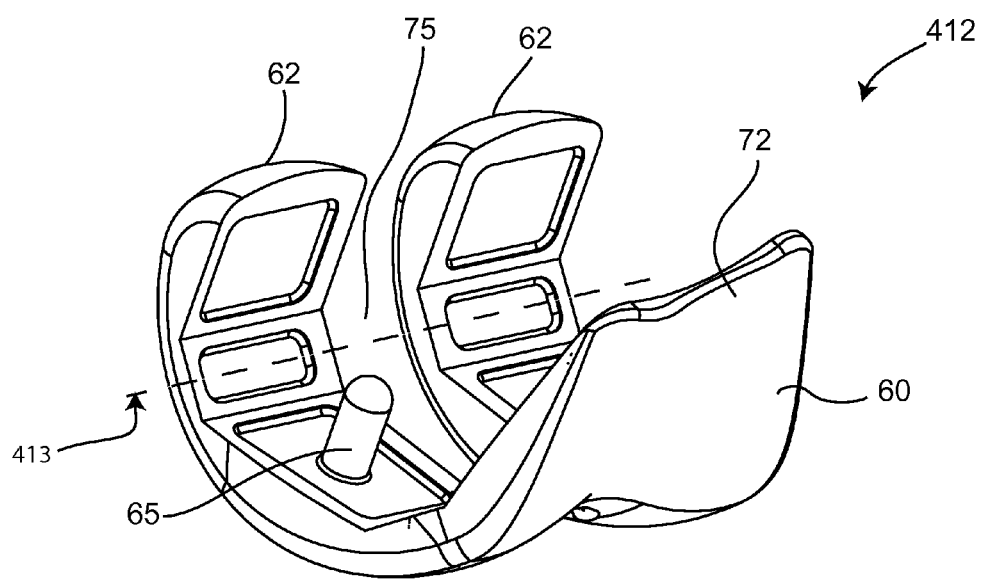
FIG. 36 illustrates a perspective view of the femoral implant of FIG. 33 with a first and second condyle, a gap and a femoral keel.
Figure 36:
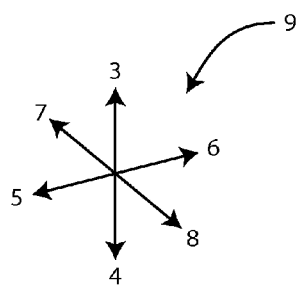

Referring to FIG. 36, the femoral implant 412 is rigidly attached to the resected femur 1 at the femur's distal end, using cement, force fit, bone ingrowth, bone screws or other method. In this embodiment the femoral implant 412 is made of a cobalt-chromium alloy; other materials suitable for this component include titanium alloys and ceramics, such as alumina or zirconia. A combination of materials may also be used. The femoral implant 412 is supported and guided by the tibial insert 416. Much like the previously disclosed femoral implant 12, this alternate embodiment of the femoral implant 412 includes a first condyle 58 and a second condyle 59 which extend posteriorly to a posterior end 62 of the femoral implant 412. During early to mid knee flexion (which may be the first 60 degrees of knee flexion in this embodiment) this motion takes the form of rotation about an axis 413, which may be a condylar axis about which the circular profiles of the condylar contact areas surround. The femoral implant 412 includes many of the features previously disclosed herein including the bone facing surface 66 and the trochlear groove 72 on the anterior end 60 of the femoral implant 412. This embodiment also includes at least one femoral keel 65 which may be circular in cross section (however, any geometric shape will do) which may extend from the bone facing surface 66 and penetrate the resected femur 1 providing greater security of the femoral implant 412 to the femur 1. The at least one femoral keel 65 may comprise two keels, one on each of the condyles 58, 59 extending from the bone facing surface 66 extending into the femur 1. The femoral implant 412 may also comprise a gap 75 bounded by the anterior end 60 and the condyles 58, 59. The gap 75 lies between the condyles and is configured to allow a natural PCL to pass through and be sustained without much interference from the femoral implant 412 or the prosthesis 410 as a whole. This embodiment of the femoral implant 412 does not have a cam feature for a cam post to interact with. Rather the gap 75 extends from the anterior end 60 to the posterior ends 62 of the first and second condyles 58, 59 and the gap 75 separates or runs between the first and second condyles 58, 59 as well. The first condyle and second condyles 58, 59 may curve cephalically, to match the contours of a natural distal end of a femur and are shaped to align with a first articulating surface 446 and a second articulating surface 447 of the tibial insert 416 respectively. The radius of curvature of the condyles 58, 59 may relatively match the same curvature of the articulating surfaces 446, 447 of the tibial insert 416. The condyles 58, 59 may be of various widths, sizes and curvatures depending on the specific anatomy of the patient or tibial insert 416. The surface curvature of the condyles 58, 59 may also vary to match the curvature of the specific tibial insert 416 chosen for the patient's mobility requirements.

Figure 37:
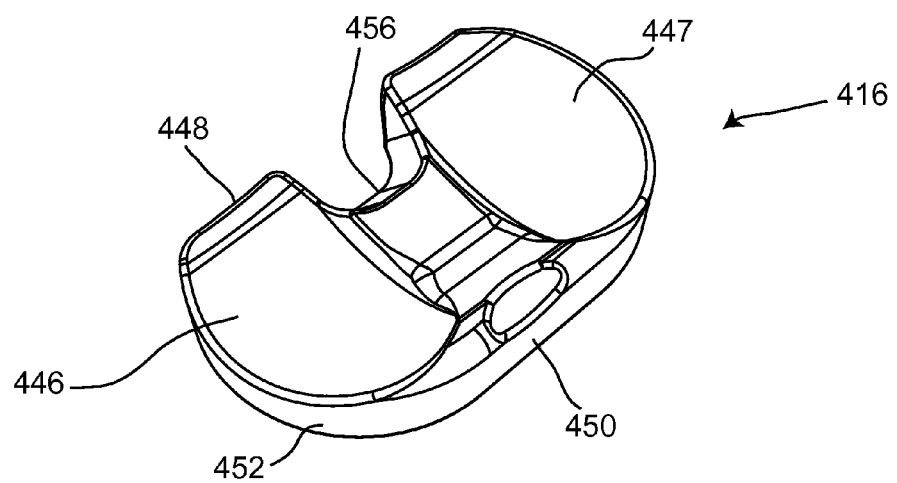
FIG. 37 illustrates a top perspective view of the tibial insert of FIG. 33 with a first and second articulating surface and a tibial insert cutout.
Figure 37:
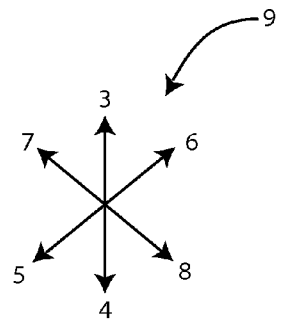
Figure 38:
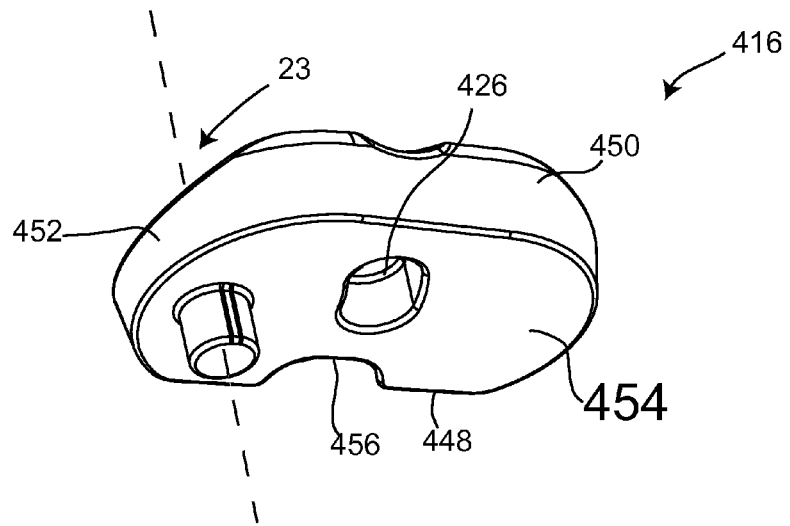
FIG. 38 illustrates a bottom perspective view of the tibial insert of FIG. 37 with a tibial baseplate facing side a tibial insert channel and a boss.
Figure 38:
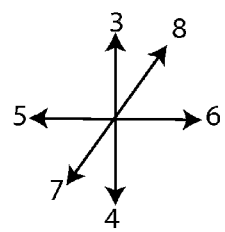

Referring to FIGS. 37 and 38, an alternate embodiment of the tibial insert 416 may comprise a medial or first articulating surface 446 and a lateral or second articulating surface 447 which interact with the first and second condyles 58 and 59 respectively. The first and second articulating surfaces 446, 447 may also support the femoral implant 412. The first and second articulating surfaces 446, 447 have a complimentary radius of curvature to accept the first and second condyles 58, 59 of the femoral implant 412. The first and second articulating surfaces 446, 447 are bounded by a tibial insert periphery 452. The tibial insert periphery 452 extends around a body of the tibial insert 416. The tibial insert periphery 452 comprises an anterior facing portion 450 and a posterior facing portion 448. The tibial insert 416 may also comprise a more pronounced tibial insert cutout 456 than that as previously described. In this embodiment the tibial insert cutout 456 may extend more anteriorly into the body of the tibial insert 416 without intersecting a central axis of the tibial insert 416. The cutout 456 may provide for a greater area to maintain the natural PCL without much interference from the prosthesis 410.

Similar to the tibial inserts already disclosed herein this tibial insert also comprises a tibial baseplate facing side 454 and a tibial insert boss 424 extending inferiorly, and positioned toward the medial side of the tibial insert 416. The tibial insert boss 424 may rotationally mate with the cavity 22 of the tibial baseplate 14. In this, and other embodiments, the axis of rotation of the tibial insert 416 is located in the first articulating surface 446. A tibial insert channel 426 may pass through a geometric center of the tibial insert 416. The tibial insert channel may pass at least partially through the tibial insert 416 and may pass entirely there through. The tibial insert channel 426 may be arc-like shaped and may be centrally located extending from the tibial baseplate facing side 454 and is shaped to slidably fit over the post 419. The post 419 provides stops for the rotation of the tibial insert 416 as it rotates about the rotational axis 23. The tibial insert 416 is preferentially made of either a cobalt-chromium alloy or polyethylene; however any other metal, polymer, ceramic, or composite, or combination may also be used.

Rollback is facilitated by the natural PCL. With the current prosthesis 410, as the knee flexes, the PCL causes the femoral implant 412 and the femur 1 to move in a posterior direction. Because of the conforming contact between the condyles 58, 59 and the articulating surfaces 446, 447 on the tibial insert 416, the tibial insert 416 also rotates in a posterior direction. This produces a knee motion very similar to the motion observed in the normal knee.

Figure 39:
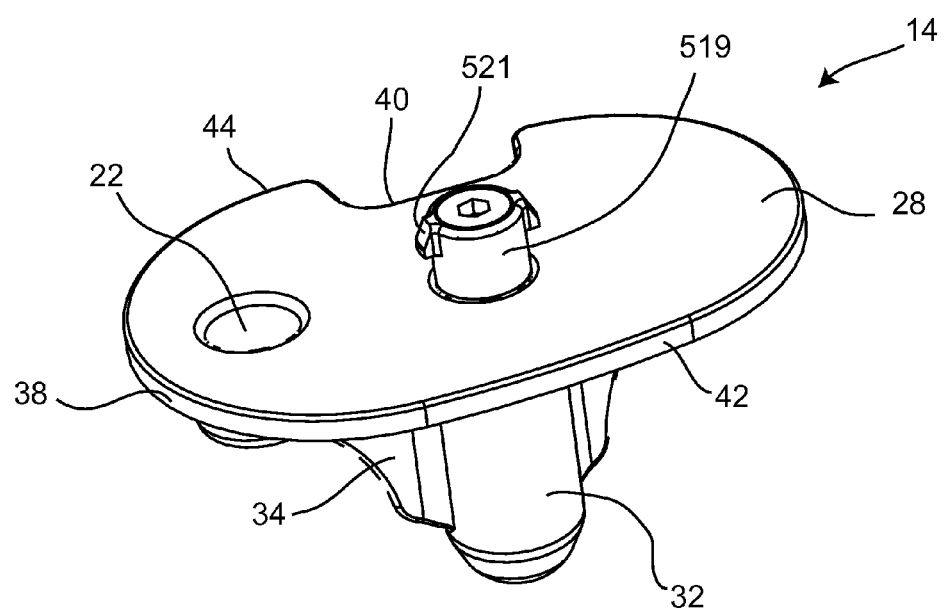
FIG. 39 illustrates a perspective view of the tibial baseplate of FIG. 34 with a alternate post and snap feature on the post.
Figure 39:
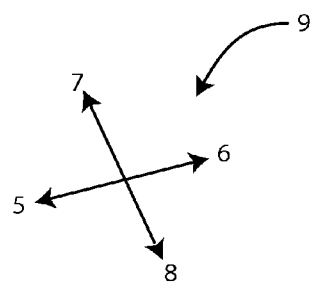
Figure 40:
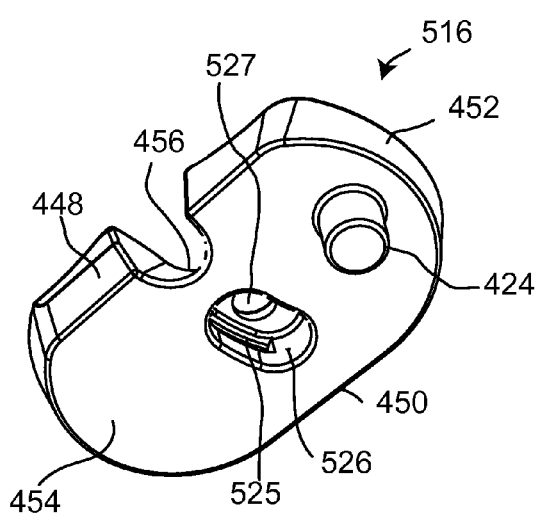
FIG. 40 illustrates a perspective view a tibial insert substantially similar to the tibial insert of FIG. 38, however, this figure illustrates a slot feature in the tibial insert channel for engaging the snap feature of the post of FIG. 39.
Figure 40:
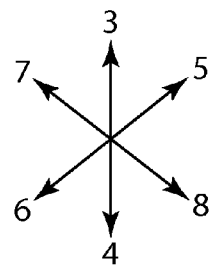
Figure 41:
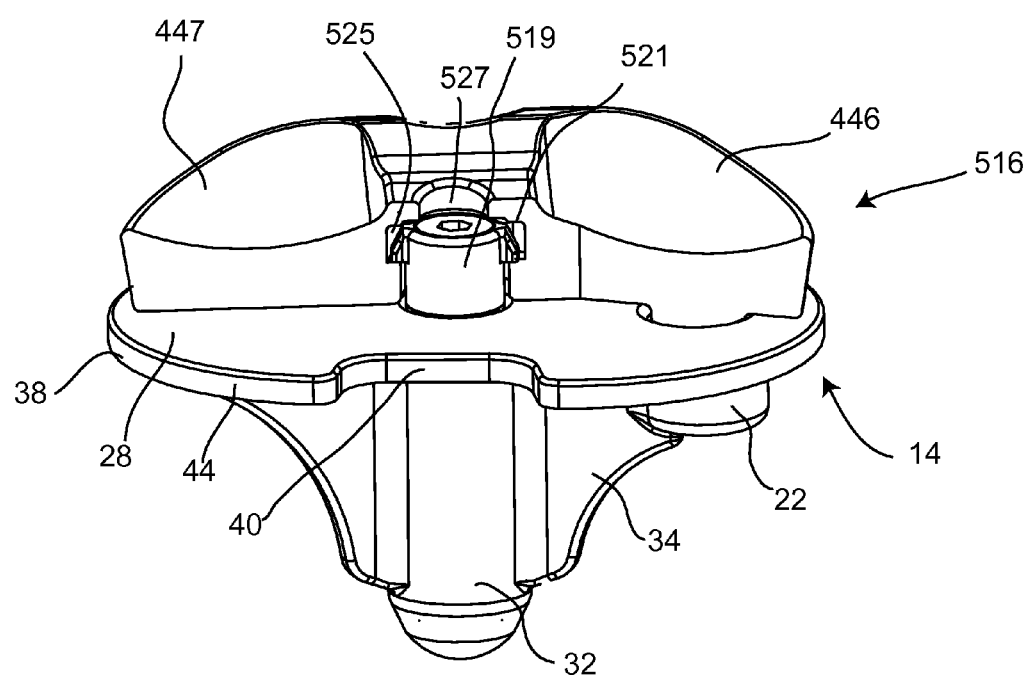
FIG. 41 illustrates a side perspective view of the tibial baseplate of FIG. 39 and the tibial insert of FIG. 40 in cross-section engaging the tibial baseplate with the snap feature and slot.
Figure 41:
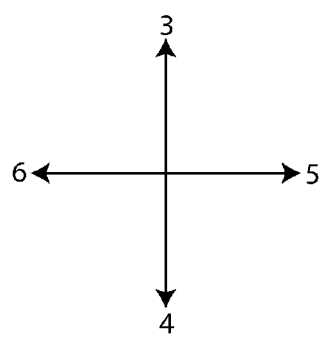

Referring to FIGS. 39-41, an alternate embodiment of a post 519 may comprise at least one feature 521, which may be a snap feature, which interacts with an alternate embodiment of a tibial insert 516 which may comprise at least one slot 525 for receiving the feature 521. All other features of the post 519, tibial baseplate 14, and tibial insert 516 are substantially the same as those previously described herein; however these alterations may be used with reference to all the different embodiments described.

Referring to FIG. 39, the feature 521 may extend from the superior point of the post 519; the feature 521 may extend in any direction non-parallel to the longitudinal axis of the post 519. FIG. 39 shows the feature 521 extending in either a medial or lateral direction. The feature 521 may deflect as it passes through a portion of a tibial insert channel 526 before entering the slot 525 of the tibial insert 516; however, the feature 521 may also be firm without deflection. The tibial insert channel 526 may pass at least partially through the tibial insert 516 and may pass entirely there through. The tibial insert channel 526 may be arc-like shaped and may be centrally located extending from the tibial baseplate facing side 454 and is shaped to fit over the post 519. The tibial insert channel 526 may comprise a taper toward the superior end of the tibial insert channel 526. The taper may terminate in an access hole 527 with a smaller cross-sectional diameter than the cross-sectional diameter of the tibial insert channel 526. The access hole may allow for limited access by an instrument or tool to be inserted into the tibial insert channel 526.

Another possible insertion method of the post 519 into the tibial insert 516 is that the feature 521 may not deflect and the tibial insert 516 is turned at an angle to allow passage of the post 519 and feature 521 without engaging the slot 525. After the post enters the tibial insert channel 526 the tibial insert 516 may be rotated into alignment with the tibial baseplate 14 wherein the feature 521 engages the slot 525. In either of the two aforementioned embodiments, the feature may alternately engage the tibial insert 516 on the superior facing surface of the tibial insert 516 between the articulating surfaces 446, 447 instead of engaging a defined slot.

Within the tibial insert channel 526 lies the at least one slot 525 for receiving the snap feature 521. The slot 525 may extend into the body of the tibial insert 516 in a medial or lateral direction, complimentary to the feature 521 to provide a capture for the feature 521 extending from the post 519. The slot may be elongated in a posterior-anterior orientation within the tibial insert channel 526 to allow the post to slidably engage the tibial insert channel 526 to allow some arc-like rotation of the tibial insert 516 during rotation of the tibial insert 516 about the axis of rotation 23; the post 519 providing a stop for the rotation of the tibial insert 516. FIG. 40 shows the slot 525 extending in a medial or later direction to correspond with the direction of the feature 521 in FIG. 39. The slot 525 may be positioned anywhere along the longitudinal axis of the tibial insert channel 526 within the tibial insert channel 526 provided that the slot 525 is capable of capturing the feature 521 to fixedly engage the tibial insert 516 to the tibial baseplate 14.

The feature 521 may be reversibly engaged to the tibial insert 516 as well and the tibial insert 516 can be disengaged from the tibial baseplate 14 if necessary. To remove the tibial insert 516 from the tibial baseplate 14 a user may pull on the tibial insert 516 to overcome the feature 521, or a removal tool may be inserted in the tibial insert channel 526 in the top of the tibial insert 516 to facilitate removal of the tibial insert 516 alone or removal of the post 519 along with the tibial insert 516. If removal of the post 519 is necessary, similar to the previous embodiment of the post 419, a threaded removal tool may be screwed into the post bore 417. The taper 478 may work as an anti-rotation feature on the post 519, with a complimentary feature on the tibial baseplate 14, to aid in removal.

FIG. 41 illustrates the interaction of the feature 521 with the slot 525 with the tibial insert 516 in cross section. The feature 521 engages with the slot 525 after passing through a portion of the tibial insert channel 526. The post 519 may terminate prior to entering the access hole 527 which may be simply because the post 519 has a greater cross sectional diameter than the cross sectional diameter of the access hole 527 which may prevent it from extending further into the tibial insert channel 526. However, the access hole 527 could have the same cross-sectional diameter as the tibial insert channel 526 and the extension of the post 519 within the tibial insert channel 526 is limited simply by the length of the post 519 protruding from the flat superior surface 28 of the tibial baseplate 14. Another limitation of the post 519 extension may be by the fit of the feature 521 and the slot 525 the feature 521 interacts with.

One other embodiment may include how the feature 521 interacts with the slot 525. The slot 525 may instead include projections which extend into the tibial insert channel 526 and the feature 521 on the post 519 may comprise grooves that interact with the projections in a similar manner as previously described but simply reversed.

One alternate embodiment of each of the aforementioned embodiments is that posts 419 and 519 may also be integrated into the body of the tibial baseplate thus making the post 419, 519 and tibial baseplate 14 one component instead of two components.

One potential advantage of all the embodiments of the above described embodiments is the use of exclusively hard materials such that wear particle generation can be reduced, reducing the chance of implant loosening. However, to be able to use exclusively hard materials requires a fully guided design—meaning a design in which relative motion between any two parts occurs along only one path which is provided in this disclosure. This is achieved with what is disclosed herein by creating two independent motion paths, in each of which motion occurs about only one axis. The first motion path is along the condylar axis 413 between the femoral implant 412 and the tibial insert 416; the second is along the rotation axis 23 in the cavity 22 of the tibial baseplate 14 as the cavity 23 interacts with the tibial insert boss 424.

Many alternative embodiments and variations exist and can be used in different combinations. One alternate embodiment is to vary the shapes of the contact surfaces, the articulating surfaces and the condyles, between the femoral implant 412 and the tibial insert 416, and/or the shapes of the contact surfaces, the superior surface and the tibial baseplate facing side, between the tibial insert 416 and the tibial baseplate 14. One alteration may be to apply a posterior slope to one or more of these surfaces, either over the entire surface or a portion. If a slope is applied to a portion of one of these surfaces, it is expected that sloping the lateral portion will be more effective in assisting natural knee motion. These sloping surfaces can be planar, curved, helical, or another shape. The methods previously described may be used with the embodiments described and illustrated in FIGS. 33-41 as well.

Other embodiments of this device would include the use of different materials and/or coatings. In addition to the materials of the those embodiments disclosed herein—cobalt chrome alloys and polyethylene—materials such as titanium and titanium alloys, nitinol, stainless steel, PEEK, and other metals, polymers or composites could be used, in any combination, in any of the embodiments of this device. Also, surface treatments to improve the wear and friction properties of wear surfaces may be added. One example of this type of surface treatment is titanium nitride; other coatings could have the same beneficial effect. Surface treatments to encourage bony attachment such as porous coatings, hydroxyapatite, and TCP may also be included in any of the aforementioned embodiments. Furthermore, surface treatments or additives in one or more of the materials used in this device could be used to provide beneficial effects such as anti-microbial, analgesic, anti-inflammatory, or other therapeutic properties.

The present device may be embodied in other specific forms without departing from its spirit or essential characteristics. It is appreciated that various features of the above described examples and embodiments may be mixed and matched to form a variety of other combinations and alternatives; for example, using the cam post 19 with the tibial insert 116 or using tibial insert 516 with post 419. It is also appreciated that this system should not be limited simply to total knee prosthesis. As such, the described embodiments are to be considered in all respects only as illustrative and not restrictive. The scope of the device is, therefore, indicated by the appended claims rather than by the foregoing description. All changes which come within the meaning and range of equivalency of the claims are to be embraced within their scope.

The invention claimed is:

1. A knee replacement system comprising:
a tibial baseplate comprising a tibia facing surface and a superior surface, wherein the superior surface defines a cavity positioned medially on the superior surface;
a femoral implant comprising a cam feature, a pair of condyles and a femur facing surface;
a tibial insert comprising a tibial baseplate facing side, a femoral implant facing side, a lateral articulating surface, and a medial articulating surface, and wherein the tibial baseplate facing side defines a boss positioned medially on the tibial baseplate facing side that is rotatable within the cavity to enable a pivotal articulation of the tibial baseplate facing side with the superior surface about a medially-displaced axis, wherein each of the medial and lateral articulating surfaces are shaped and positioned to articulate with the pair of condyles;
the tibial insert further comprising an arc-shaped channel passing through the tibial baseplate facing side of the tibial insert, the arc-shaped channel tibial being concave toward the medial articulating surface; and
a post protruding from the superior surface and passing through the arc-shaped channel, wherein the pivotal articulation is provided at least partially by contact of an anterior side of the cam feature with a posterior side of the post during articulation of the pair of condyles with the medial and lateral articulating surfaces.

2. The knee replacement system of claim 1, wherein the channel passes through the tibial baseplate facing side of the tibial insert along a direction non-parallel to the baseplate facing side.

3. The knee replacement system of claim 1, wherein the superior surface further comprises a hole, wherein the post comprises an inferior end received in the hole, wherein the inferior end comprises a taper.

4. The knee replacement system of claim 3, wherein the post comprises a post bore at a superior end, wherein the post bore is configured to receive a screw, wherein the screw is fixedly attached to the post.

5. The knee replacement system of claim 4, further comprising:
a first snap feature on the superior end of the post configured to engage a first slot in the channel of the tibial insert.

6. The knee replacement system of claim 5, wherein the first snap feature is deflectable, wherein the channel deflects the first snap feature before the first snap feature engages the first slot.

7. The knee replacement system of claim 6, wherein the superior end of the post further comprises a second snap feature and the channel further comprises a second slot.

8. The knee replacement system of claim 5, wherein the channel is bounded by a continuous wall which defines the arc shape of the channel.

9. The knee replacement system of claim 4, wherein the femoral implant facing side of the tibial insert overlaps the superior end of the post, wherein an access hole extends between the femoral implant facing side and a superior end of the channel, wherein the diameter of the superior end of the post is greater than the diameter of the access hole so that the superior end of the post is prevented from protruding through the access hole.

10. The knee replacement system of claim 9, wherein the diameter of the access hole is less than the medial-lateral width of the channel.

11. The knee replacement system of claim 4, wherein the inferior end of the post comprises a notch and the hole comprises a surface shaped to provide a key fit with the notch, wherein the notch prevents rotation of the post within the hole.

12. The knee replacement system of claim 1, wherein each of the condyles comprises a radius of curvature defining flexion and extension of a knee joint in which the knee replacement system is implanted, wherein each of the medial and lateral articulating surfaces comprises a radius of curvature closely matched to that of the corresponding condyle such that a center of rotation of each condyle remains substantially stationary relative to the corresponding articulating surface during flexion and extension of the knee joint.

13. The knee replacement system of claim 1, wherein the femoral implant further comprises a gap between the pair of condyles, wherein the gap receives the posterior cruciate ligament when operatively assembled.

* * * * *